US012318186B2

(12) United States Patent
Pimentel et al.

(10) Patent No.: US 12,318,186 B2
(45) Date of Patent: Jun. 3, 2025

(54) BREATH GAS ANALYSIS

(71) Applicant: CEDARS-SINAI MEDICAL CENTER, Los Angeles, CA (US)

(72) Inventors: Mark Pimentel, Los Angeles, CA (US); Kapil Gupta, Los Angeles, CA (US); Ali Rezaie, Beverly Hills, CA (US); Nicholas David Allan, Victoria (CA); Kristofor Dyck Dolberg, Victoria (CA); Nigel Anthony Syrotuck, Victoria (CA); Martin Juergen Kellinghusen, Victoria (CA); Mark Sasha Drlik, Victoria (CA); Nathan John Muller, Victoria (CA); Kenneth MacCallum, Victoria (CA)

(73) Assignee: Cedars-Sinai Medical Center, Los Angeles, CA (US)

( * ) Notice: Subject to any disclaimer, the term of this patent is extended or adjusted under 35 U.S.C. 154(b) by 621 days.

(21) Appl. No.: 17/124,101

(22) Filed: Dec. 16, 2020

(65) Prior Publication Data
US 2021/0177303 A1 Jun. 17, 2021

Related U.S. Application Data

(60) Provisional application No. 62/949,057, filed on Dec. 17, 2019.

(51) Int. Cl.
*A61B 5/083* (2006.01)
*A61B 5/00* (2006.01)
(Continued)

(52) U.S. Cl.
CPC ............ *A61B 5/0836* (2013.01); *A61B 5/082* (2013.01); *A61B 5/087* (2013.01); *A61B 5/097* (2013.01);
(Continued)

(58) Field of Classification Search
None
See application file for complete search history.

(56) References Cited

U.S. PATENT DOCUMENTS

| 5,291,898 A | 3/1994 | Wolf |
| 6,364,938 B1 | 4/2002 | Birbara et al. |

(Continued)

FOREIGN PATENT DOCUMENTS

| AU | 2016315721 A1 | 8/2022 |
| BR | 11-2018-004097 A2 | 4/2018 |

(Continued)

OTHER PUBLICATIONS

Ajibola et al., Effects of dietary nutrients on volatile breath metabolites, Journal of Nutritional Science, 2013, vol. 2, e34, pp. 1-15.
(Continued)

*Primary Examiner* — Michael R Bloch
(74) *Attorney, Agent, or Firm* — Nixon Peabody LLP

(57) ABSTRACT

Systems and methods have been developed for implementation of a breath testing system for convenient sampling of intestinal gases exhaled from a patient's breath. This may include a system with a manifold that includes thermal regulation components, for instance thermistors and resistive heating elements, which maintain the temperature of the gases above the body temperature of the patient. In some examples, the system will determine an indication of whether a patient has SIBO by adjusting a change in exhaled hydrogen concentration by a methane level exhaled by a patient.

26 Claims, 21 Drawing Sheets

(51) Int. Cl.
  *A61B 5/08* (2006.01)
  *A61B 5/087* (2006.01)
  *A61B 5/097* (2006.01)
  *A61B 8/00* (2006.01)
  *G01N 33/497* (2006.01)

(52) U.S. Cl.
  CPC .......... *A61B 5/4255* (2013.01); *A61B 5/7275* (2013.01); *A61B 5/742* (2013.01); *A61B 8/546* (2013.01); *A61B 2560/02* (2013.01); *A61B 2560/0266* (2013.01); *A61B 2560/0462* (2013.01); *A61B 2562/0271* (2013.01); *A61B 2562/06* (2013.01); *G01N 33/497* (2013.01)

(56) References Cited

U.S. PATENT DOCUMENTS

| | | | |
|---|---|---|---|
| 7,048,906 B2 | 5/2006 | Lin et al. | |
| 7,288,136 B1 | 10/2007 | Gray et al. | |
| 8,383,026 B1 | 3/2013 | Leubke et al. | |
| 8,500,854 B1 | 8/2013 | Pennline et al. | |
| 8,821,614 B1 | 9/2014 | Albenze et al. | |
| 9,050,579 B1 | 6/2015 | Wickramanayake et al. | |
| 9,066,962 B2 | 6/2015 | Pimentel et al. | |
| 9,186,854 B1 | 11/2015 | Luebke et al. | |
| 9,192,618 B2 | 11/2015 | Pimentel et al. | |
| 9,358,245 B2 | 6/2016 | Pimentel et al. | |
| 10,066,254 B2 | 9/2018 | Pimentel et al. | |
| 10,844,417 B2 | 11/2020 | Pimentel et al. | |
| 11,103,157 B2 | 8/2021 | Gupta et al. | |
| 2002/0039599 A1* | 4/2002 | Lin ..................... | A61K 31/201 |
| | | | 514/18.1 |
| 2004/0147038 A1 | 7/2004 | Lewis et al. | |
| 2004/0186391 A1* | 9/2004 | Pierry .................... | A61B 5/083 |
| | | | 600/532 |
| 2006/0074335 A1 | 4/2006 | Ben-Oren et al. | |
| 2006/0246045 A1 | 11/2006 | Pimentel et al. | |
| 2008/0045825 A1 | 2/2008 | Melker et al. | |
| 2008/0138320 A1 | 6/2008 | Pimentel et al. | |
| 2008/0182291 A1 | 7/2008 | Pimentel et al. | |
| 2009/0233888 A1 | 9/2009 | Lin | |
| 2011/0009764 A1 | 1/2011 | Lanier et al. | |
| 2011/0023581 A1 | 2/2011 | Chou et al. | |
| 2011/0302992 A1 | 12/2011 | Robbins et al. | |
| 2012/0150056 A1 | 6/2012 | Christman et al. | |
| 2012/0234076 A1 | 9/2012 | Rigas | |
| 2012/0285320 A1 | 11/2012 | Heald et al. | |
| 2013/0165810 A1* | 6/2013 | Saatchi .................. | A61B 5/097 |
| | | | 600/537 |
| 2014/0206636 A1 | 7/2014 | Lin et al. | |
| 2014/0228431 A1 | 8/2014 | Pimentel et al. | |
| 2015/0099713 A1 | 4/2015 | Pimentel et al. | |
| 2017/0055875 A1 | 3/2017 | Candell et al. | |
| 2017/0074857 A1* | 3/2017 | Dennis ................. | A61B 5/4848 |
| 2017/0191953 A1 | 7/2017 | Rigas | |
| 2018/0249929 A1 | 9/2018 | Nakagawa et al. | |
| 2018/0271404 A1* | 9/2018 | Gupta ..................... | A61B 5/082 |
| 2019/0136286 A1 | 5/2019 | Pimentel et al. | |
| 2020/0064330 A1 | 2/2020 | Pimentel et al. | |

FOREIGN PATENT DOCUMENTS

| | | |
|---|---|---|
| CA | 2996425 A1 | 3/2017 |
| CL | 2018570 | 6/2018 |
| CN | 108139384 A | 6/2018 |
| EP | 1200828 B1 | 8/1999 |
| EP | 2267445 A1 | 12/2010 |
| EP | 3344995 A1 | 7/2018 |
| IN | 201827007178 A | 2/2018 |
| KR | 20180043832 A | 4/2018 |
| MX | 20180002721 A | 4/2018 |
| NZ | 740135 | 11/2020 |
| WO | 2017/040546 A1 | 3/2017 |
| WO | WO-2018156937 A1 * | 8/2018 .......... A61K 31/437 |
| WO | 2021127027 A1 | 6/2021 |

OTHER PUBLICATIONS

Lisowska et al., Small intenstine bacterial overgrowth is frequent in cystic fibrosis: combined hydrogen and methane measurements are required for its detection, Acta Biochimica Polonica, 2009, vol. 56(4), pp. 631-634.
Cowie et al., Membrane Inlet Ion Trap Mass Spectrometry for the Direct Measurement of Dissolved Gases in Ecological Samples, Journal of Microbiological Methods, 1999, vol. 35(1), pp. 1-12.
Lazik, D., Membrane Based Measurement Technology for in situ Monitoring of Gases in Soil, Sensors, 2009, vol. 9, pp. 756-767.
Saad et al., Breath Tests for Gastrointestinal Disease: The Real Deal or Just a Lot of Hot Air?, Gastroenterology, 2007, vol. 133, pp. 1763-1766.
Scarlata, K., The Complete Idiot's Guide to Eating Well with IBS, New York, NY, Penguin Group, 2010.
Wang et al., Measurement of Mercury in Flue Gas Based on an Aluminum Matrix Sorbent, The Scientific World Journal, 2011, vol. 11, pp. 2469-2479.
EP 16842833.2 Partial Search Report dated Jan. 30, 2019, 17 pages.
Written Opinion with Translation of CL 201800570 dated Apr. 12, 2019, 33 pages.
SG 11201801664P Search Report and Written Opinion dated Mar. 29, 2019, 10 pages.
EP 16842833.2 Supp Search Report dated Apr. 29, 2019, 16 pages.
ISR and WO PCT/US2016/049528 dated Feb. 1, 2017, 13 pages.
International Preliminary Report on Patentability for PCT/US2016/049528 dated Mar. 6, 2018, 7 pages.
ISR for PCT/US2020/65382 dated Mar. 9, 2021, 2 pages.
Written Opinion for PCT/US2020/65382 dated Mar. 9, 2021, 6 pages.
Supplementary Search Report of SG 11201801664P, dated Jan. 17, 2020, 3 pages.
Cloarec et al., Breath hydrogen response to lactulose in healthy subjects: relationship to methane producing status. Gut, Mar. 1, 1990, vol. 31, No. 3, pp. 300-304.
First Examination Report IP No. 740135 dated Sep. 27, 2019, 3 pages.
CL Office Action Search Report dated Jul. 20, 2020, 3 pages.
CL Written Opinion dated Jul. 20, 2020, 12 pages.
Notice of Preliminary Rejection dated Jun. 29, 2023, 13 pages.
Saad et al., Breath Testing for Small Intestinal Bacterial Overgrowth: maximizing Test Accuracy, Clinical Gastroenterology and Hepatology 2014(12):1964-1972.
Sachdeva et al., Small intestinal bacterial overgrowth (SIBO) in irritable bowel syndrome: frequency and predictors, Journal of Gastroenterology and Hepatology, 2011, vol. 26(3), pp. 135-138.
Extended European Search Report for 20904094.8 dated Nov. 12, 2023, 9 pages.
Gouma et al., Sensing device for breath biomarker detection, 2019 IEEE International Symposium on Olfaction and Electronic Nose, May 26, 2019, pp. 1-3, XP033611802.
Singer-Englar et al., a novel 4-gas device for breath testing shows exhaled H2S is associated with diarrhea and abdominal pain in a large scale prospective trial, Gastroenterology, Elsevier Inc., US, 154(6), May 1, 2018, XP085389780, 1 page.
BR Examination Report for BR112018004097 dated May 6, 2024, 8 pages.
Pimentel et al., Methanogens in human health and disease, American Journal of Gastroenterology supplements, 2012, 1:28-33.
Moraes do Nascimento, FLoT: an agent-bsed framework for self-adaptive and self-organizing internet of things aplications. Dissertation presented to the Programa Postgraduate course in Informatics of the Department of Information Technology at the Scientific Technical Center of PUC-Rio, Lucena, Rio de Janeiro, Aug. 2015, 102 pages.

* cited by examiner

|  | N or Mean | % or Std. dev | Median |
|---|---|---|---|
| Age (year)[a] | 49.0 | 16.9 | 47.5 |
| BMI (kg/m$^2$)[b] | 24.7 | 5.7 | 23.6 |
| Female | 196 | 65.8 | - |
| *Diagnosis* | | | |
| IBS | 120 | 40.3 | - |
| Constipation | 133 | 44.6 | - |
| Ulcerative colitis | 12 | 4.0 | - |
| Crohn's disease | 21 | 7.1 | - |
| History of intestinal infection | 19 | 6.4 | - |
| *Other Measurements* | | | |
| Had breath test at Cedars-Sinai within last year | 54 | 18.2 | - |
| Experienced weight loss | 87 | 29.6 | - |
| Blood in stool | 16 | 7.2 | - |
| *Symptoms by VAS Measurements* | | | |
| Bloating | 66.3 | 26.6 | 71.0 |
| Excess gas | 62.5 | 26.7 | 68.0 |
| Incomplete evacuation | 52.1 | 31.2 | 59.0 |
| Abdominal pain | 55.6 | 28.9 | 62.0 |
| Constipation | 46.7 | 31.5 | 50.5 |
| Diarrhea | 43.8 | 32.2 | 48.0 |
| Urgency with bowel movement | 44.5 | 32.1 | 49.0 |
| Discharge of mucus from rectum | 26.4 | 29.0 | 12.0 |
| Straining during bowel movement | 43.3 | 29.9 | 49.5 |
| Fatigue | 58.0 | 27.8 | 64.0 |
| Belching | 43.7 | 31.4 | 46.5 |
| Hoarseness or a problem with voice | 24.3 | 27.6 | 10.0 |
| Clearing the throat | 34.5 | 30.2 | 26.0 |
| Excess throat mucus or postnasal drip | 40.5 | 33.1 | 40.0 |
| Difficulty swallowing food, liquid, or pills | 23.1 | 27.7 | 9.0 |
| Coughing after eating or lying down | 23.2 | 27.4 | 10.0 |
| Breathing difficulties or choking episodes | 18.3 | 23.2 | 8.0 |
| Troublesome or annoying cough | 21.3 | 26.0 | 9.0 |
| Sensation of something sticking in the throat or lump in the throat | 28.6 | 30.3 | 14.0 |
| Heartburn, chest pain, indigestion, or stomach acid coming up | 45.9 | 31.4 | 51.0 |

[a] Age range: 19-88 years.
[b] BMI range: 15.7-54.1 kg/m$^2$

FIG. 12

|  | $H_2S$ Negative (<1.2ppm) | $H_2S$ Positive (≥1.2 ppm) | Prob.* |
|---|---|---|---|
| *Symptoms* | Mean±SD | Mean±SD |  |
| Abdominal pain | 54.4±28.3 | 59.1±30.7 | 0.10 |
| Bloating | 66.6±26.8 | 65.2±26.2 | 0.63 |
| Constipation | 47.0±31.4 | 45.9±31.9 | 0.86 |
| Diarrhea | 41.2±31.8 | 52.1±32.4 | 0.01 |
| Discharge of mucus from rectum | 26.5±29.3 | 25.9±28.2 | 0.83 |
| Excess gas | 63.1±26.7 | 60.8±26.6 | 0.55 |
| Incomplete evacuation | 51.9±31.9 | 52.4±29.2 | 0.97 |
| Straining during bowel movement | 42.1±30.0 | 47.0±29.5 | 0.23 |
| Urgency with bowel movement | 42.3±31.7 | 51.4±32.4 | 0.04 |
| *Symptom Combinations* |  |  |  |
| Diarrhea + Urgency with bowel movement | 41.8±28.2 | 51.8±29.2 | 0.01 |
| Abdominal pain + Diarrhea | 47.8±23.8 | 55.6±24.3 | 0.01 |
| Abdominal pain + Diarrhea + Urgency with bowel movement | 46.0±23.8 | 54.2±24.0 | 0.01 |
| *Probability is calculated by Wilcoxon test | | | |

FIG. 13

|  | Negative test (%) | Positive test (%) |
|---|---|---|
| $H_2$ | 116 (39%) | 182 (61%) |
| $CH_4$ | 237 (80%) | 61 (20%) |
| $H_2S$ | 226 (76%) | 72 (24%) |

FIG. 14

BREATH GAS ANALYSIS

CROSS REFERENCE TO RELATED APPLICATIONS

This application claims priority to U.S. Provisional Application No. 62/949,057 filed Dec. 17, 2019, titled BREATH GAS ANALYSIS, the contents of which are incorporated herein by reference.

FIELD OF THE INVENTION

The present invention is directed to systems and methods for analyzing the gases exhaled in the breath of a patient.

BACKGROUND OF THE INVENTION

The following description includes information that may be useful in understanding the present invention. It is not an admission that any of the information provided herein is prior art or relevant to the presently claimed invention, or that any publication specifically or implicitly referenced is prior art.

The human gastro-intestinal system is home to billions of bacterial cells that typically aid in digestion, but can be harmful if they grow too prolifically. These bacteria feed on the foods ingested by humans and produce both useful and harmful by-products. Bacteria are usually thousands of times less prevalent in the small intestine than in the large intestine. However, in some patients experiencing small intestine bacterial overgrowth ("SIBO"), the number of bacteria in the small intestine increase to the point that they approach the quantities of the large intestine. SIBO causes excessive gas production which can create discomfort and uncomfortable symptoms in a patient. For instance, a patient with excessive gas production may experience abdominal pain, bloating, excessive burping, flatus, discomfort generally and nausea. SIBO is thought to affect a significant number (some 10%) of adults.

Research (such as that disclosed in U.S. Pat. No. 8,388,935) has drawn an extensive but imperfectly-defined relationships between SIBO and numerous conditions such as irritable bowel syndrome (IBS), fibromyalgia, chronic pelvic pain syndrome, depression, impaired mentation, halitosis, tinnitus, sugar craving, autism, attention deficit/hyperactivity disorder, drug sensitivity, an autoimmune disease, and Crohn's disease. Using the tools currently available, caregivers have been able to correlate SIBO with some of these conditions in certain patients. Unfortunately, however, each patient's bacterial landscape is fairly unique, and therefore, universal correlations are difficult, if not impossible, to achieve. Accordingly, single tests in a laboratory are rarely determinative for diagnostic purposes.

Concentrations of $CH_4$ and $H_2$ exhaled in the breath have been shown in numerous studies to be linked to SIBO, though it appears that every patient is affected somewhat differently. For instance, concentrations in the ranges of $CH_4$ (~1-50 ppm) and $H_2$ (~1-50 ppm) have been shown to be clinically significant.

Furthermore, excessive methane production has been shown to be associated with obesity and excess gas production has been shown to be associated with irritable bowel syndrome. Recently, there has been a higher level of interest in SIBO due to its possible link with irritable bowel syndrome. Furthermore, higher levels of methane are indicative of SIBO that causes constipation. See FIG. 1.

Currently, SIBO is diagnosed using a predetermined diet regime prior to a lab test of the exhaled gases of the patient. For example, the patient may take a dose of carbohydrate such as lactulose (typically 10 g) or glucose (typically 50 g). Then, after ingestion, samples of the patient's breath are analyzed for hydrogen, typically every 15-20 minutes for up to 3 hours. Where the patient is administered glucose a rise in hydrogen concentration, typically >10 ppm (parts per million) above the baseline level is indicative of a positive test.

Lactulose is a sugar that is digested by colonic bacteria and not by the human host. The ingested lactulose should pass through the small intestine undigested and reach the colon where the bacteria produce gas. In the normal individual, there is a single peak of gas in the breath following the ingestion of lactulose when the lactulose enters the colon. Individuals with SIBO may produce two significant peaks of gas in the breath. The first abnormal peak occurs as the lactulose passes the gas-producing bacteria in the small intestine, and the second normal peak occurs as the lactulose enters the colon. If the baseline levels of hydrogen rise by >20 ppm after ingestion of lactulose, this can also indicate a positive test. Recently, a number of studies have demonstrated the limitations of the use of lactulose in diagnosing SIBO, mainly because of the high rate of false positives. Hydrogen breath testing may be able to diagnose only 60% of patients with SIBO. There has been much less work undertaken on combined methane/hydrogen detection for improving SIBO diagnoses. Even less so is work to measure hydrogen sulfide, and hydrogen sulfide in combination with methane and hydrogen detection.

Thus there remains a need in the art for a device or system for measuring these hydrogen, methane, and hydrogen sulfide, individually or in combinations.

SUMMARY

Accordingly, consumption of certain foods has been shown to be linked to increased gas production which is linked to a variety of illnesses including SIBO. However, the precise foods and quantities responsible for excessive gas production in each individual are burdensome to determine. For instance, in order to test for SIBO, an individual must come to a lab for a test of the gases or breathe into a bag and send it in for analysis. It is thus impractical to test the exhaled gases of the patient over many different meals and over a longer period of time.

Therefore, because intestinal gases must be tested in isolated cases, and usually after a high sugar meal, most individuals cannot determine or correlate SIBO or its symptoms to specific food items. Accordingly, it is difficult to acquire enough information on the gases produced in a particular individual to form conclusions about the food consumption patterns likely leading to excessive gas production. There is thus a need for a portable, SIBO testing device that a patient could use to frequently test their breath gas levels while simultaneously enter and store information about the time and content of meals consumed prior to testing. With this information and appropriate data analysis, the patients will then be able to discover correlations between the foods they eat and their SIBO symptoms and gas levels.

Accordingly, systems and methods have been developed for implementation of a portable SIBO testing system for convenient sampling of intestinal gases exhaled from a patient's breath. These devices may be in the form of a hand held meter that would integrate with a smartphone or other device with an application that can record data relating to food consumed by a user.

Additionally, systems and methods have been developed to accurately test the gases using a clinical grade testing device. In some examples, this includes a system using a manifold to maintain the temperature of the exhaled breath gases as they flow through the channels of the manifold. In some examples, the system uses gas sensors with probes that test the content of the exhaled gases as they pass through the channels of the manifold. In some examples, the system may utilize thermistors and resistive heating elements connected to a printed circuit board to heat the channel and/or the manifold to maintain the exhaled gasses at a temperature above body temperature to prevent condensation or humidity from damaging the sensors or biasing the readings of the gas concentrations.

In some examples, the disclosed technology provides an ex vivo method of sensing gas concentration in exhaled breath, the method comprising: receiving a batch of exhaled breath from a patient; heating the batch of exhaled breath to a temperature above 37 degrees Celsius while pumping the air through a flow path at a constant flow rate; sensing gas concentrations in the flow path using a set of electrochemical sensors; and displaying the gas concentrations.

It will be appreciated that the methods of this example and all of the other methods disclosed herein are suitable to be conducted as ex vivo methods. In such embodiments, the various steps of the method are not all practiced on the patient's body. The skilled person wishing to practice the invention will be aware of many ways in which the methods of the invention may be conducted ex vivo.

It will be recognized that the reference to "receiving a batch of exhaled breath from a patient" does not require the batch of breath that is to undergo the further steps of the method to be received directly from the patient into the recited flow path. Instead, the batch of exhaled breath may be received "indirectly", for example via collection in a suitable container, passageway, and the collected batch then subject to the further steps of the method ex vivo. A suitable container may, for example, be selected from the group consisting of a breath bag, balloon, conduit, passageway, breathing tube or other suitable device, container or passageway.

For the avoidance of doubt, ex vivo embodiments of the methods of the invention specifically encompass those in which the batch of exhaled breath from the patient is no longer in fluid communication with the patient when undergoing further steps of the method. For example, the batch of breath may no longer be in fluid communication with the patient when it is present within the recited flow path. Suitably, the batch of breath may be collected by means of a mask, container, bag, tube, or other such apparatus attached to the patient, but, at the time that the batch is within the flow path and subject to further steps of the method, the batch may no longer be in fluid communication with the mask or patient. Such separation of the batch may be achieved by any appropriate devices, features and processes. It will be appreciated that in such embodiments, since the batch of exhaled breath undergoing analysis is no longer in direct communication with the patient, the recited steps of the method are not practiced on the human body.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 1 depicts, in accordance with various embodiments of the present invention, a bar graph showing the importance of Methane in MO Diagnosis (prior art).

FIG. 12 depicts, in accordance with various embodiments of the present invention, a table illustrating subject demographics of an example study using the present technology.

FIG. 13 depicts, in accordance with various embodiments of the present invention, a table illustrating a comparison of symptoms based on the presence or absence of $H_2S$.

FIG. 14 depicts, in accordance with various embodiments of the present invention, a table illustrating breath test result using an example of a four gas device as disclosed herein.

FIG. 19A shows all subjects and FIG. 19B has outliers removed.

Figure 1A:
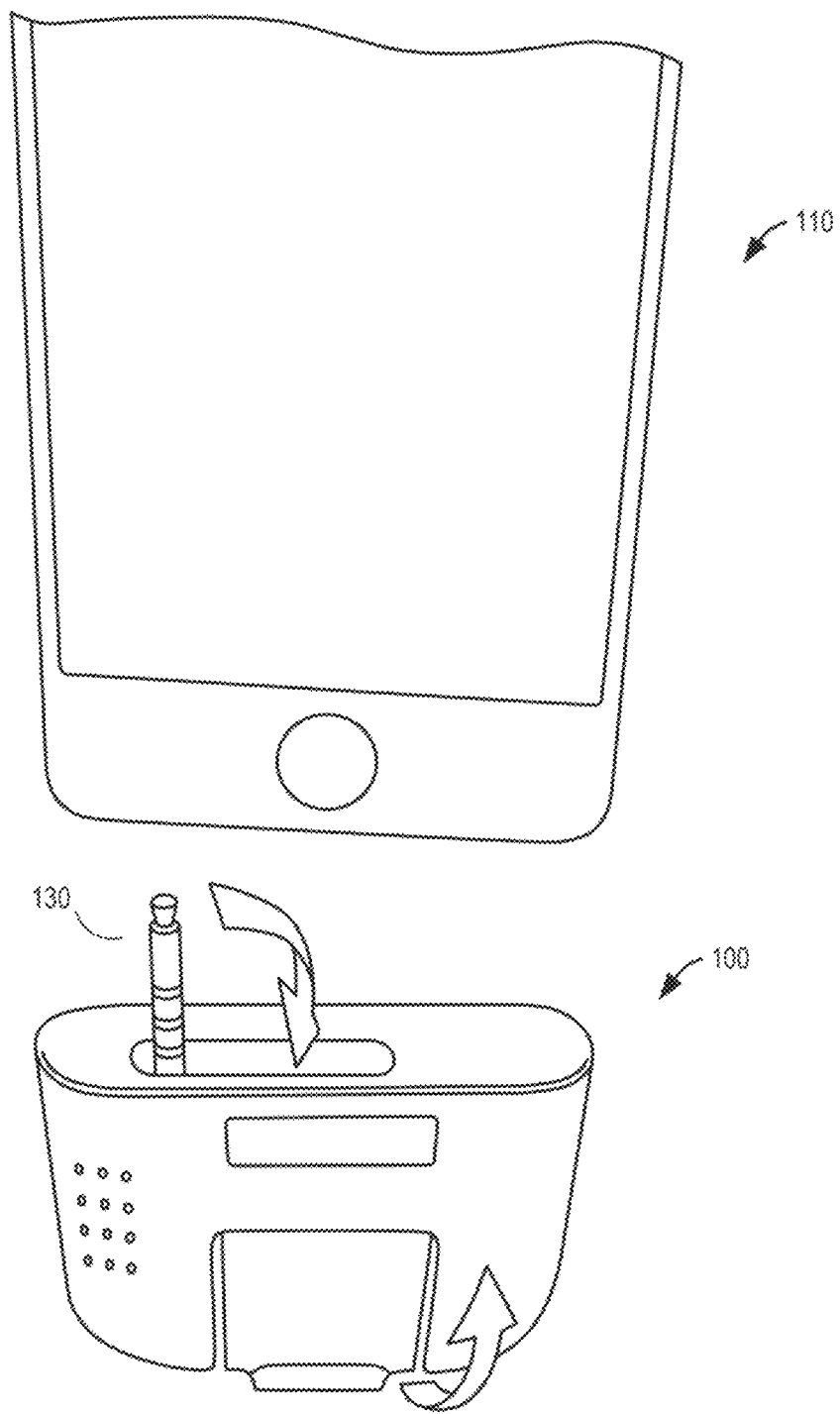
FIG. 1A depicts, in accordance with various embodiments of the present invention, a perspective view of a gas detection device that interfaces with a mobile device.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

As described above, consumption of certain foods has been shown to be linked to increased gas production which is linked to a variety of illnesses including SIBO. However, the precise foods and quantities responsible for excessive gas production in each individual are difficult to determine. For instance, in order to test for SIBO an individual must come to a lab for a test of the gases or breathe into a bag and send it in for analysis. Therefore, it is impractical to test the exhaled gases of the patient over many different meals and over a longer period of time.

Therefore, because intestinal gases must be tested in isolated cases, and usually after a prescribed, high sugar meal, most individuals cannot determine or correlate SIBO or its symptoms to specific food items, quantities and times. Accordingly, it is difficult to acquire enough information on the gases produced in a particular individual to form conclusions about the food consumption patterns likely leading to excessive gas production. Therefore, there is a need for a portable, SIBO testing meter for home or clinical use that a patient could use to test after a variety of meals and time points, and simultaneously log information about the time and content of meals consumed prior to testing.

A device allowing for frequent use would provide users a system to frequently and consistently monitor their exhaled gas and associated bacterial levels. With this information and appropriate data analysis, the users will then be able to discover correlations between the foods they eat and their SIBO symptoms and gas levels.

Accordingly, systems and methods have been developed for a gas testing device (e.g. portable SIBO testing meter) for convenient testing of intestinal gases exhaled from a patient's breath. These devices may be in the form of a hand held meter that would integrate with a smartphone or other device with an application or other software that can record data relating to food consumed by a user.

Additionally, systems and methods have been developed to accurately test the gases using a clinical grade testing device. In some examples, this includes a system that uses a manifold to maintain the temperature of the exhaled breath gases as they flow through the channels of the manifold. In some examples, the system uses gas sensors with probes that test the content of the exhaled gases as they pass through the channels of the manifold. In some examples, the system may utilize thermistors and resistive heating elements connected to a printed circuit board to heat the channel and/or the manifold to maintain the exhaled gasses at a temperature above body temperature to prevent condensation or humidity from damaging the sensors or biasing the readings of the gas concentrations.

This is particularly advantageous, because the system does not require desiccants, sorbents or other absorbent technology to remove moisture. Additionally, the humidity levels are more consistent and this allows more accurate readings throughout the manifold, which allows a greater number of sensors to be utilized, including all four breath gas sensors that include $CO_2$, $H_2$, $CH_4$, and $H_2S$ sensors, so that all four gases can be tested at once. In some examples, the manifold and sensor integration advantageously allow for measuring all four gases at the same time in the same device, while getting accurate and consistent readings.

Breath Intake Device

In some embodiments, the breath sampling systems disclosed herein may include a breath intake device for measuring the flow and directing the gases to the components that measure the levels of gases. In some embodiments, these may include a tube or other structure. In another example, the device may include a quartz microbalance. In another example, the gas volume may be measured via a colorimetric assay and/or by tin oxide. In another example, the device may contain individual cartridges in order to detect specific gases. For example, the device may contain individual cartridges for $CO_2$, $CH_4$, and/or $H_2S$ respectively. The cartridges may be disposable such that the device may last for multiple uses (e.g., 300 readings) and or a predetermined amount of time (e.g., 1-2 years). In another example, each disposable cartridge may last for a number of uses (e.g., 10-50 readings) and/or a predetermined amount of time (e.g., 1-3 months).

In some embodiments, devices and methods disclosed herein may include a flow control and moisture control module 880, to prevent moisture and variations in the flow and partial pressures of gases from skewing the results. This may include heating elements that heat the channels of the devices to at our above body temperature in some examples. Additionally, the device may include a backflow prevention mechanism so that exhaled air is does not escape and remains isolated for testing. Moisture control may be included before or after the flow regulator to adjust the air humidity to a consistent level or to remove all moisture if sensor cross-sensitivities exist, or to prevent general moisture contamination.

The carbon dioxide sensor, which may work in conjunction with the flow sensor, is then exposed to the air to quantify the lung air volume that is passed through the device (with exhaled air nominally at 4% $CO_2$ and not largely influenced by SIBO levels.

Portable Hydrogen Device

In some embodiments, a small, portable device is disclosed. In some embodiments, the portable device may utilize an electrochemical sensor to measure $H_2$ and may also have a method of normalization such as $CO_2$ detection. In some embodiments, the device may communicate and send data to a smartphone via Bluetooth, USB, cellular, or other connection transmit its data for processing and display. In some embodiments, the device can also be built as an iPhone attachment, physically attaching to the device.

Portable Clinical Device

In some embodiments, a clinical grade, handheld analysis device may be utilized that can detect $CO_2$, $H_2$, $CH_4$, and $H_2S$ using durable and reusable sensors. In some embodiments, it may operate from a rechargeable battery. In some embodiments, $CO_2$ could be detected using an NDIR cell, and $H_2S$ could be detected with a fuel cell sensor. $H_2$, as in some embodiments, can be detected with an Alphasense electrochemical cell or equivalent.

In some embodiments, it can connect to a smartphone app via Bluetooth to upload data. That data would be processed both on the smartphone and by cloud servers that also have the ability to share results with healthcare providers. The device would also accept user inputs such as time stamped activities and clinically relevant symptoms.

Full Clinical Device

In some embodiments, disclosed is a clinical medical device capable of detecting $CO_2$, $H_2$, $CH_4$, and $H_2S$ with a high degree of accuracy. It may use electrochemical sensors, a Gas Chromatograph, Ion Mobility Spectrometer, TDLS, or a Flame Ionization Detector, or a combination of these technologies or others. As with the other devices, readings would be available very shortly after a sample passed through the detector. Some of these comprehensive sensor technologies might be expensive and would be more amenable to being a centralized tool to which samples are sent.

For this embodiment, the patient may blow into a breath collector, or as an alternate embodiment, the clinician could attach a bag to the connector or gas inlet that the patient has filled previously by blowing into the bag. After analysis, the data would be printed off or sent to a PC, and the clinician may be required to run a purging gas (e.g. for re-calibration and/or clearing of the breath gases) through the device (such as inert nitrogen, or another gas with a precise $H_2S$, $H_2$, $CO_2$ and $CH_4$ concentration).

Computer Application

The devices disclosed herein may interface with various computing devices that are configured with instructions to allow entry and storage of data relating to consumption of food and/or to operate the various components, heating systems, flow motors and meters and other components. An essential tool for both the home and clinical devices will be the associated software applications in the form of a smartphone app or other software program. The device will either connect to the smartphone via Bluetooth or hardwire, allowing data transfer. The application will connect to the internet to perform some combination of updates, cloud data storage, or information processing. A clinical version might be setup with a dedicated tablet, hardwired to the device, to display and process results.

For the home use device, the software may be implemented to help the patient make their own choices and conclusions from the data regarding how their diet affects their SIBO readings and how they should change their diet. It is also important to match activities (such as eating) with measurements in a way the patient can understand. These requirements are not a significant technical risk. Many devices with this embodiment are being engineered today, and many engineers are capable of such projects.

In some examples the software may include various control logic for maintaining a closed loop control for temperature regulation of the gas flow pathways in the device. This could include various manifold or pipes on the clinical or handheld devices with various heating elements that could heat the air.

Methods for Acquiring Data from a Patient

Various protocols may be utilized to determine when a patient is to test their gases, and what symptom and meal information a patient enters after testing. For instance, in some embodiments, the patient may only use the device when the feel the symptoms of SIBO. In those embodiments, the user interface of the application may ask the patient which of the pre-defined categories of symptoms the user is experience, for instance: bloating, constipation, diarrhea, etc.

Then, the application may request what type of food the patient ingested within the past 12 hours, 6 hours, 4 hours, 20 minutes or other relevant time frame in terms of SIBO gas production. In some embodiments, the system will have certain predefined categories of food and amounts. For instance, the program may have sugar based, fat based, or protein based food categories. In other embodiments, the program may have an index of food categories that are linked in a database to certain nutritional values or ingredients relevant to SIBO. For instance, the types of sugars in each food may be indicated, including glucose, sucrose, lactose, etc.

The system may also require and save the data in a memory, which may be shared with a server or may be saved locally. In some embodiments, the application will ask a user for information, including sex, height, weight, age, and SIBO related characteristics. This information may be utilized in the cloud to correlate similar patients' ingestion and related gases. Additionally, specific patients may create specific combinations or types of gases or have certain profiles of bacteria.

In some embodiments, the patient may undergo a lactulose or glucose breath test in order to test the gases produced in response to certain substances. The caregiver may also instruct the patient to fast for one hour, two hours or other specified time to determine a methane concentration in the breath of the patient.

Analysis of Data for SIBO and Other Correlations

In some embodiments, once the data is acquired, it may be logged for analysis by the patient. In other embodiments, the processor or associated control systems may analyze the data. For instance, the device may look in patterns of correlating symptoms to certain foods, times and/or exhaled gases. For instance, in some embodiments, the system may correlate a particular gas level (e.g. crosses a threshold level known to be abnormal or has a characteristic double spike instead of single) with eating a certain amount of a certain type of sugar within a specific amount of time. In some embodiments, machine learning algorithms may be utilized to match the types of conditions optimal for SIBO for a given patient.

In other embodiments, the correlation may be more straightforward, and correlate the frequency of SIBO symptoms with eating a certain type of foods within a predefined time window. In other embodiments, the system may correlate or determine, for instance, the average $H_2$, $H_2S$, or $CH_4$ levels or peak of the levels within a certain time windows after eating certain foods. The system could then determine whether certain classes of foods (e.g., foods containing sucrose) result in a spike of a certain gas or combination of gases above a pre-defined threshold. In other embodiments, the system could output a graph of the average and standard deviation of gas levels after eating certain types or classes of foods.

In some embodiments, the system may correlate a level of hydrogen change over time or after undergoing a lactulose or glucose regimen. Additionally, a system as disclosed herein may additional test both the hydrogen and methane before and after ingestion of sugar and lactulose to detect the change in concentration of the cases. The system could then process the data to determine a methane calibrated hydrogen change. The system could then calibrate the change in hydrogen to the current methane production for the patient to determine a more accurate indication of whether a patient has SIBO.

In some embodiments, the system may output data in the form of a chart to allow a user an easy and convenient method for analyzing the gas levels and associated foods. In some embodiments, the foods could be ranked in terms of the amount of increased gas production they result in.

Accordingly, consumption of certain foods has been shown to be linked to increased gas production which is linked to a variety of illnesses including SIBO. However, the precise foods and quantities responsible for excessive gas production in each individual are difficult to determine. For instance, in order to test for SIBO an individual must come to a lab for a test of the gases or breathe into a bag and send it in for analysis. Therefore, it is impractical to test the exhaled gases of the patient over many different meals and over a longer period of time.

EXAMPLES

Following are examples of various devices that may be utilized according to the present disclosure. These examples are not intended to be limiting, and only provide examples of various features and methods that may be employed for efficiently testing breath gases in a patient.

Figure 1B:
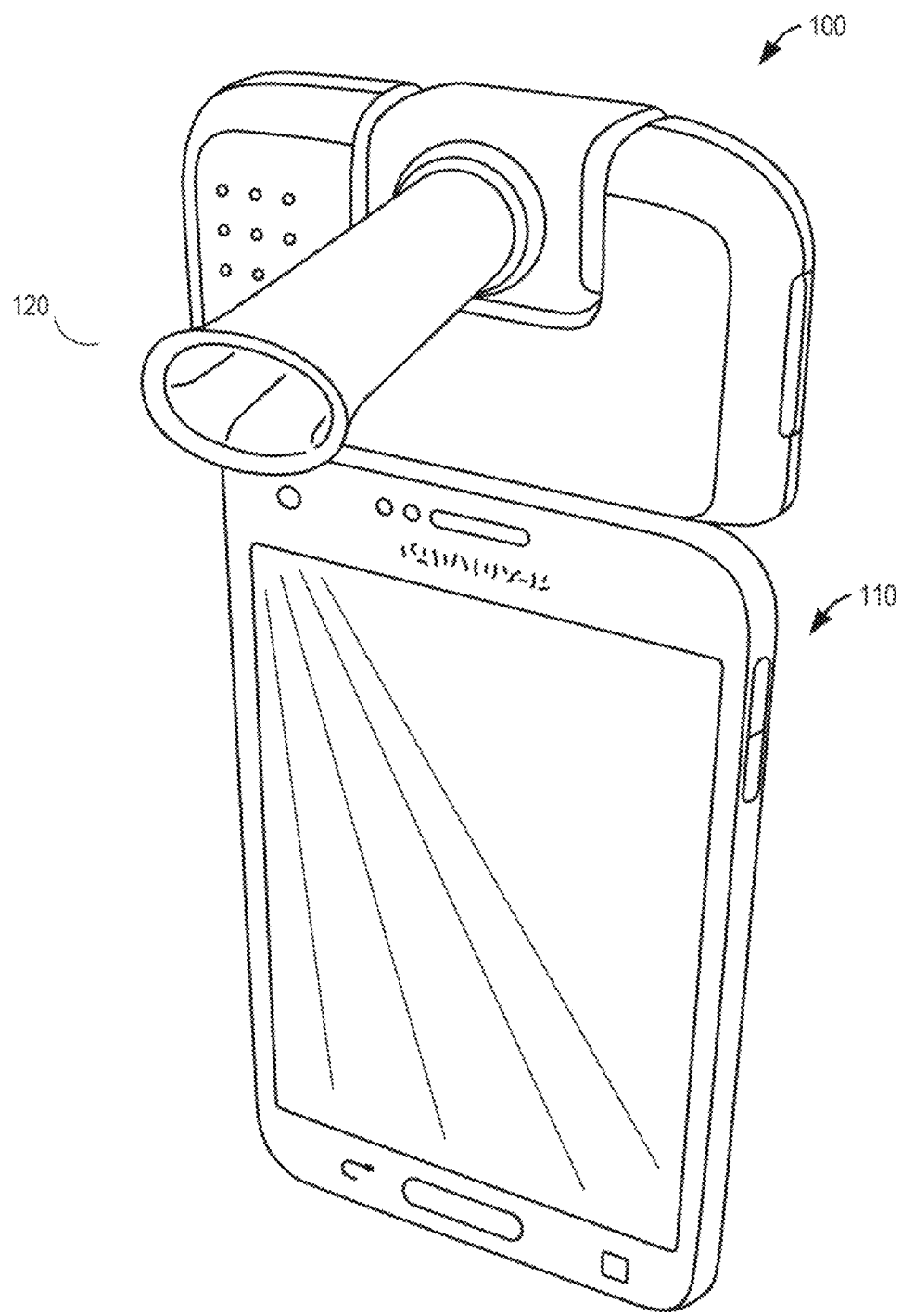
FIG. 1B depicts, in accordance with various embodiments of the present invention, a perspective view of a gas detection device that interfaces with a mobile device.

FIGS. 1A-1B illustrate an example of an embodiment of a gas detection device 100 that may be attached to a mobile device 110. The device includes a mobile interface 130, which may be any standard mobile connection for the iPhone, blackberry, other mobile phone, including standard jack (as illustrated). In some embodiments, the connection will be a Bluetooth, Wi-Fi or other wireless connection.

The device also includes a retractable mouthpiece 120 pictured in FIG. 1B or other suitable breath collection devices. In some embodiments, the connection to the mouthpiece 120 will allow the mouthpiece 120 to be removed, and the connection to be rotated into place inside the gas detection device 100. Mouthpieces may be utilized on clinical or other systems for capturing and testing breath gases as disclosed herein. In some embodiments, the mouthpiece 120 can be stored separately or replaced. This will allow the mouthpiece to remain sanitary, and easily connected for each breath test.

Figure 2:
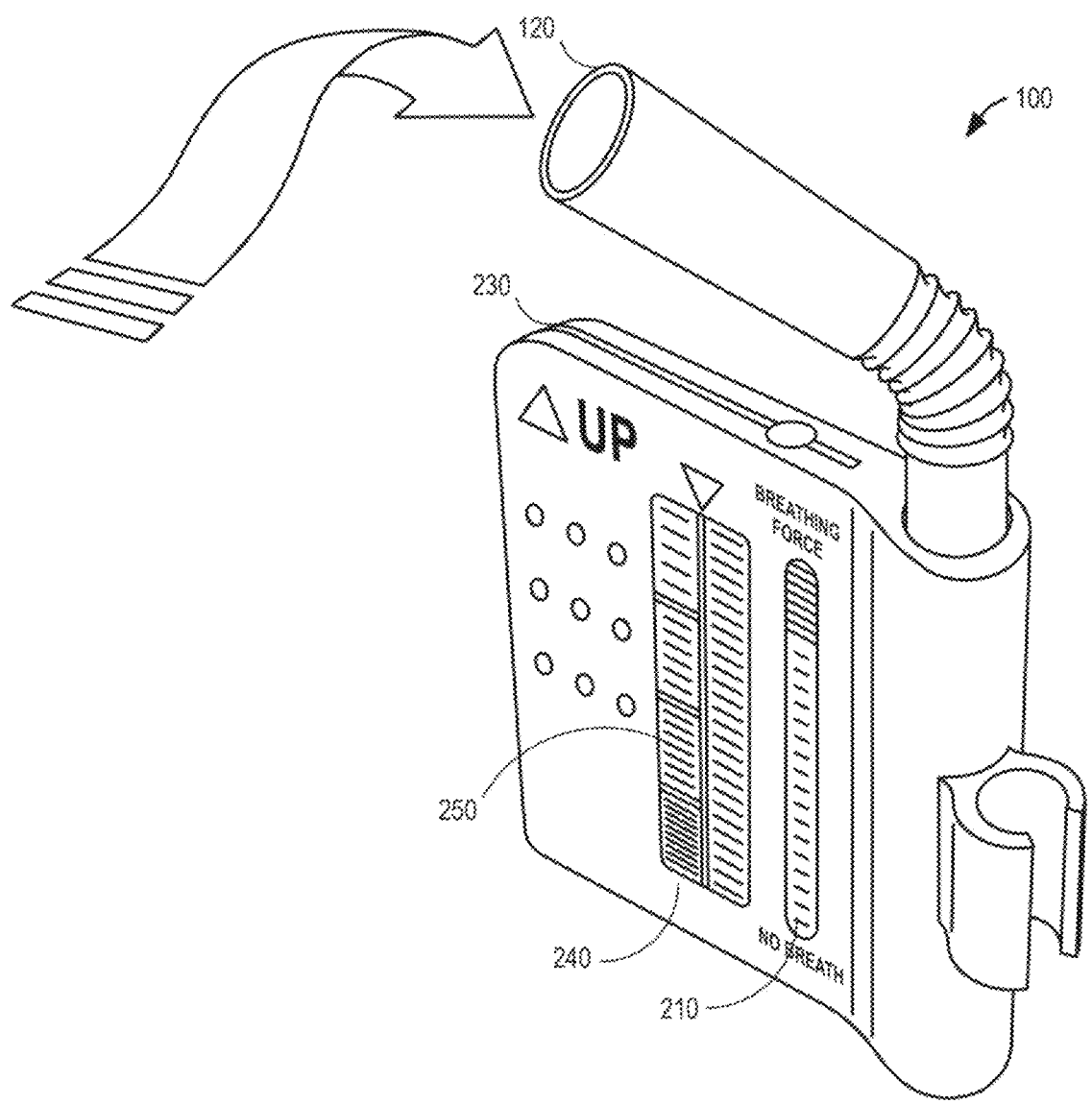
FIG. 2 depicts, in accordance with various embodiments of the present invention, a perspective view of a gas detection device.

FIG. 2 illustrates an embodiment of a gas detection device 100 that includes a mouthpiece 120 and a flow meter 210. In some embodiments, the gas detection device will utilize test strips 250 with colorimetric based gas sensing technology. In some embodiments, the test strips 250 will be inserted into an opening or slot 230 of the gas detection device 100. The device may include a display or indicator 240 indicating gas levels. In some embodiments, the test strips 250 may be visible behind a glass or plastic, transparent window that is the display 240.

When a patient breathes into the mouthpiece 120 the flow meter will provide feedback to the patient regarding the proper strength of breath. Then the test strips may change color based on the amount of gases contained in the patient's breath. Accordingly, an optical reader may translate the color change into gas concentrations or the patient may get a qualitative or quantitative assessment by visually inspecting the color change. In some embodiments, the test strips provide a threshold indication of whether the patient has gases that are indicative of SIBO or another condition (e.g., more of a binary or rudimentary measure). In other embodiments, precise gas levels will be calculated and stored.

Figure 3A:
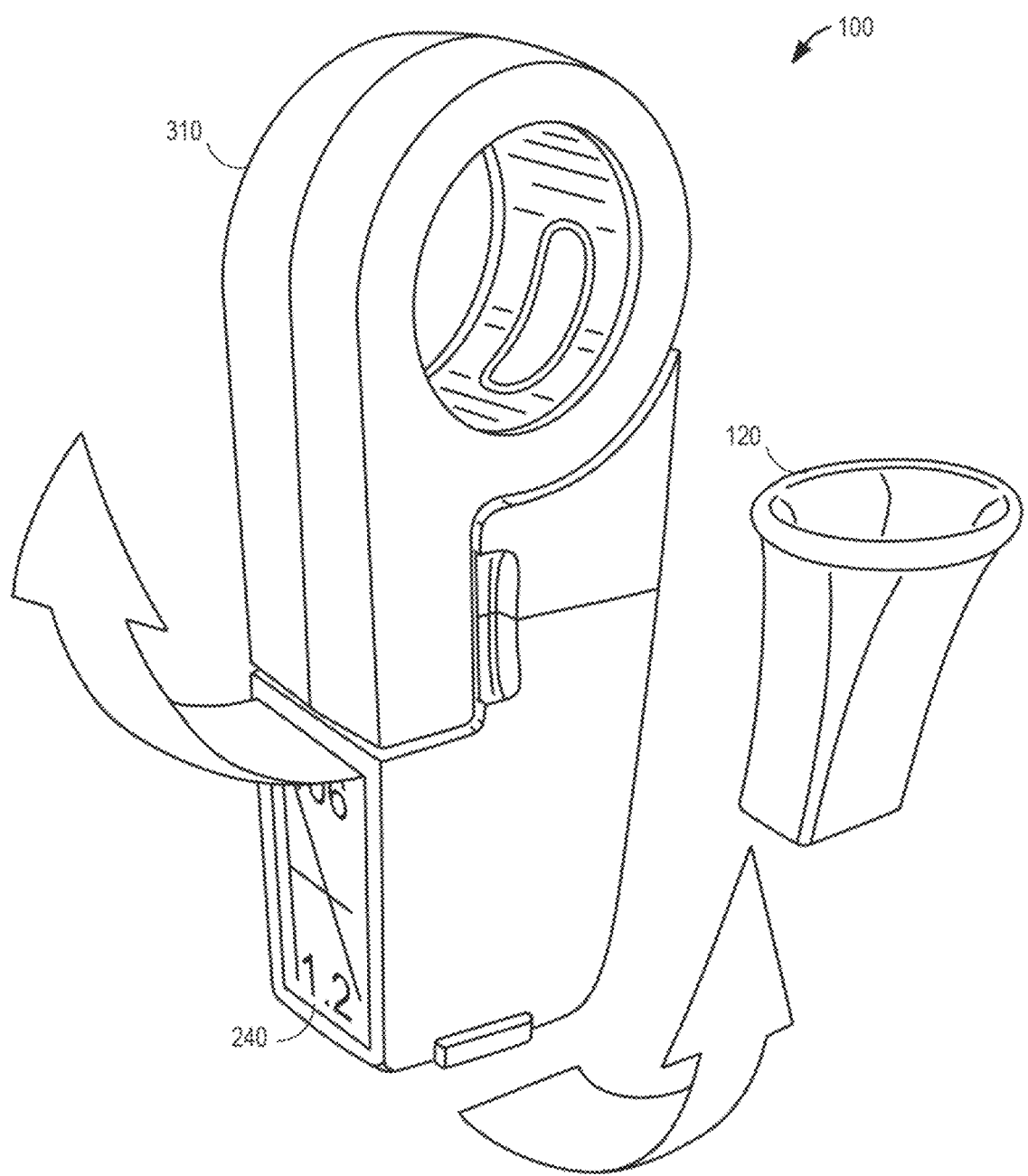
FIG. 3A depicts, in accordance with various embodiments of the present invention, a perspective view of a gas detection device.
Figure 3B:
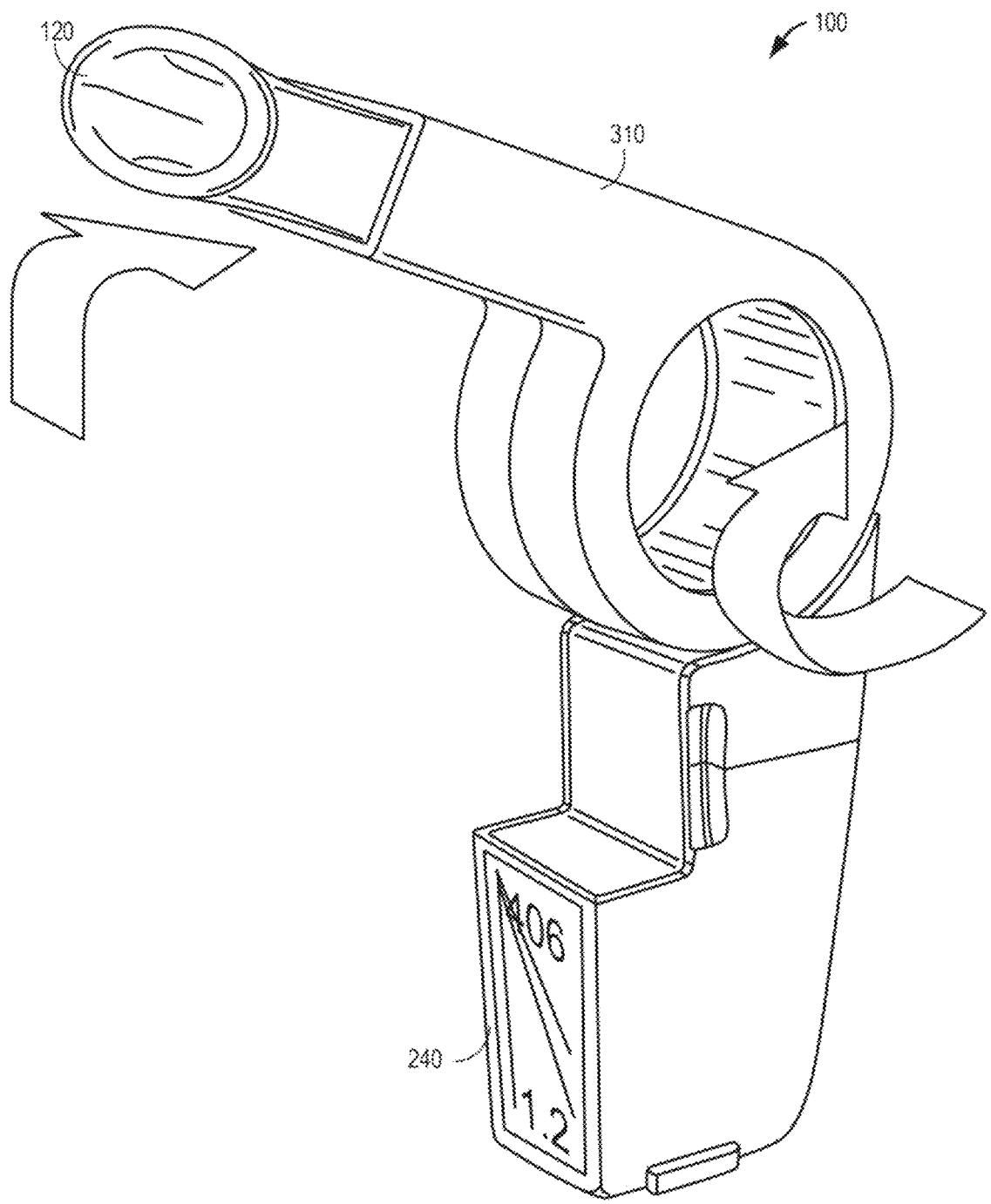
FIG. 3B depicts, in accordance with various embodiments of the present invention, a perspective view of a gas detection device.

FIGS. 3A-3B illustrate embodiments of a gas testing device 100 that include a rotatable breath collector 310 for directing the exhaled breath gases to the testing chambers and a mouthpiece 120. This embodiment includes a display 240 for displaying the results of the testing. FIG. 3B illustrates the breath collector 310 rotated out into a position in which the patient may breath into the mouthpiece 120 and breath collector 310 can then collect the breath gas. As illustrated, after rotating out the breath collector 310, the mouthpiece 120 may be attached. This rotation allows the passageways of the breath collector 310 to remain protected an inaccessible while not in use, and allows the device to remain compact. These aspects may also be added to a clinical or table top breath testing system as disclosed herein.

Figure 4:
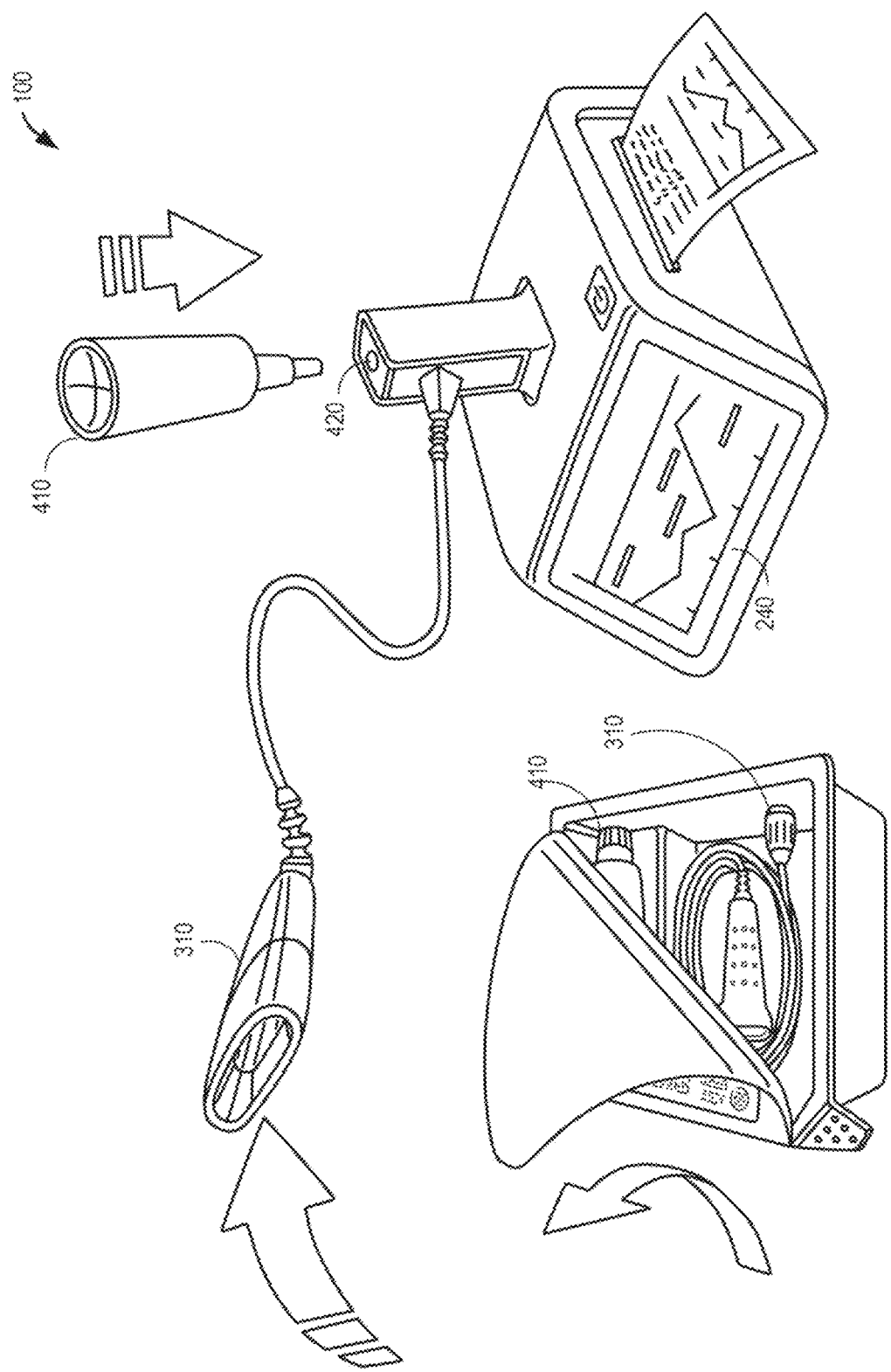
FIG. 4 depicts, in accordance with various embodiments of the present invention, a perspective view of a gas detection device and associated breath tube kit.

FIG. 4 illustrates an embodiment of a clinical gas testing device 100 that includes a breath collector 310, and a display 240. In some embodiments, the clinical gas testing device 100 may include a larger testing chamber and employ more precise and accurate sensing technology. In some embodiments, the clinical gas testing device 100 may include a purge canister 410 for purging the testing chamber of breath gases from a patient, and the purge canister 410 is coupled to the testing chamber via a purge canister receiving portion 420. This will allow the chamber to be recalibrated from a baseline gas level after each use. In some embodiments, the canister 410 and breath collector 310 will be disposable pieces, separately packaged for each use as illustrated in FIG. 4. In some embodiments, the clinical gas testing device 100 may include pipes or a manifold that are heated or have the gas in their passageways directly heated to prevent humidity or gas temperature from impacting the results.

Figure 5:
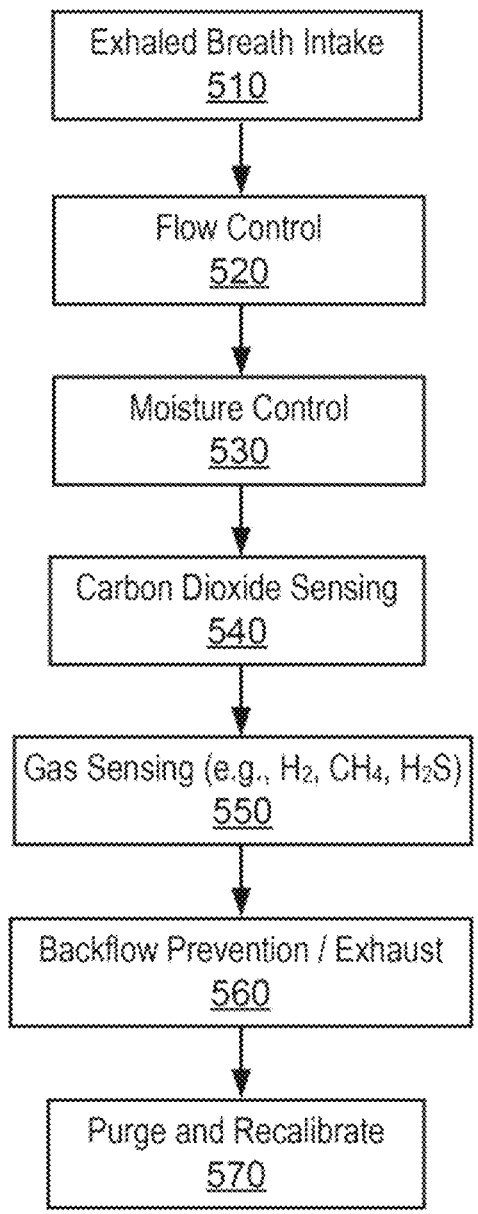
FIG. 5 depicts, in accordance with various embodiments of the present invention, a flow chart depicting a method of testing breath gases.

FIG. 5 illustrates an embodiment of a method of testing the breath gases of a patient utilizing various gas detection devices 100 as disclosed herein. For instance, first the exhaled breath is collected 510 and directed to a testing chamber. In some embodiments, a flow meter and pump may control the flow rate of the exhaled breath being routed through the testing chamber 520. This may allow the partial pressure of relevant gases to be held constant, or to otherwise increase the accuracy of the results. After, the moisture may also be controlled 530, to avoid inaccurate sensor readings that may be caused for a variety of reasons based on the gas detection technology including by utilizing heating elements as disclosed herein.

Afterward, some embodiments will include a carbon dioxide sensor 540 to use as a proxy for the amount of breath exhaled, and to correlate the levels of breath gases to the amount of $CO_2$. In some embodiments, the amount of $CO_2$ or concentration of the gas can be correlated to determine how long the air has been held in the lungs. The levels of relevant gases detected thereafter can be adjusted accordingly to the appropriate ratios.

After carbon dioxide is tested (or simultaneously or beforehand) the levels of other gases may be sensed 550 that have clinical relevancy. For example, the system may then test $H_2$, $CH_4$, and/or $H_2S$. Additionally, backflow may be prevented 560 to prevent the concentration from changing once testing has initiated in any such device. Finally, after testing, the breath gases may be purged and the device recalibrated 570. In some embodiments, the recalibration will be performed by purging the device with a canister of a gas(es) at a known concentration(s) and/or known flow rate(s). In other embodiments, a fan and door may open to allow ambient air to enter the device.

Example: Methane Calibrated Hydrogen Levels

The lactulose breath test is increasingly being used to diagnose small intestinal bacterial overgrowth (SIBO). In the last decade, data have accumulated about the importance of methane in breath testing especially in the context of constipation. During the production of methane, methanogenic archaea in the gut utilize 4 hydrogen ($H_2$) gas molecules to produce a single methane ($CH_4$). Based on this stoichiometry, the level of hydrogen on breath testing (and thus the interpretation of the breath test) could be affected when detectable methane (and hence methanogens) are present. The inventors performed a study of a large scale breath test database to determine the effect of methane on the interpretation of hydrogen results.

Consecutive patients presenting to a tertiary care medical center between November 2005 and October 2013 for lactulose breath testing were eligible for review. For the breath test, subjects presented after a 12 hour fast. After a baseline breath sample, 10 g of lactulose was administered followed by subsequent breath samples every 15 minutes for a minimum of 90 minutes. Breath samples were then analyzed on a Quintron SC or Breathtracker™ gas chromatograph (Quintron Instrument Co., Milwaukee, WI) to measure hydrogen and methane after correction for $CO_2$. Breath methane was defined as ≥3 ppm any time during test. The remaining subjects were deemed non-methane subjects. Subjects were excluded if they were non-gas producers (neither hydrogen nor methane ≥3 ppm at any time during test). Interactions between hydrogen and methane were examined by comparing methane and non-methane breath tests.

Figure 6:
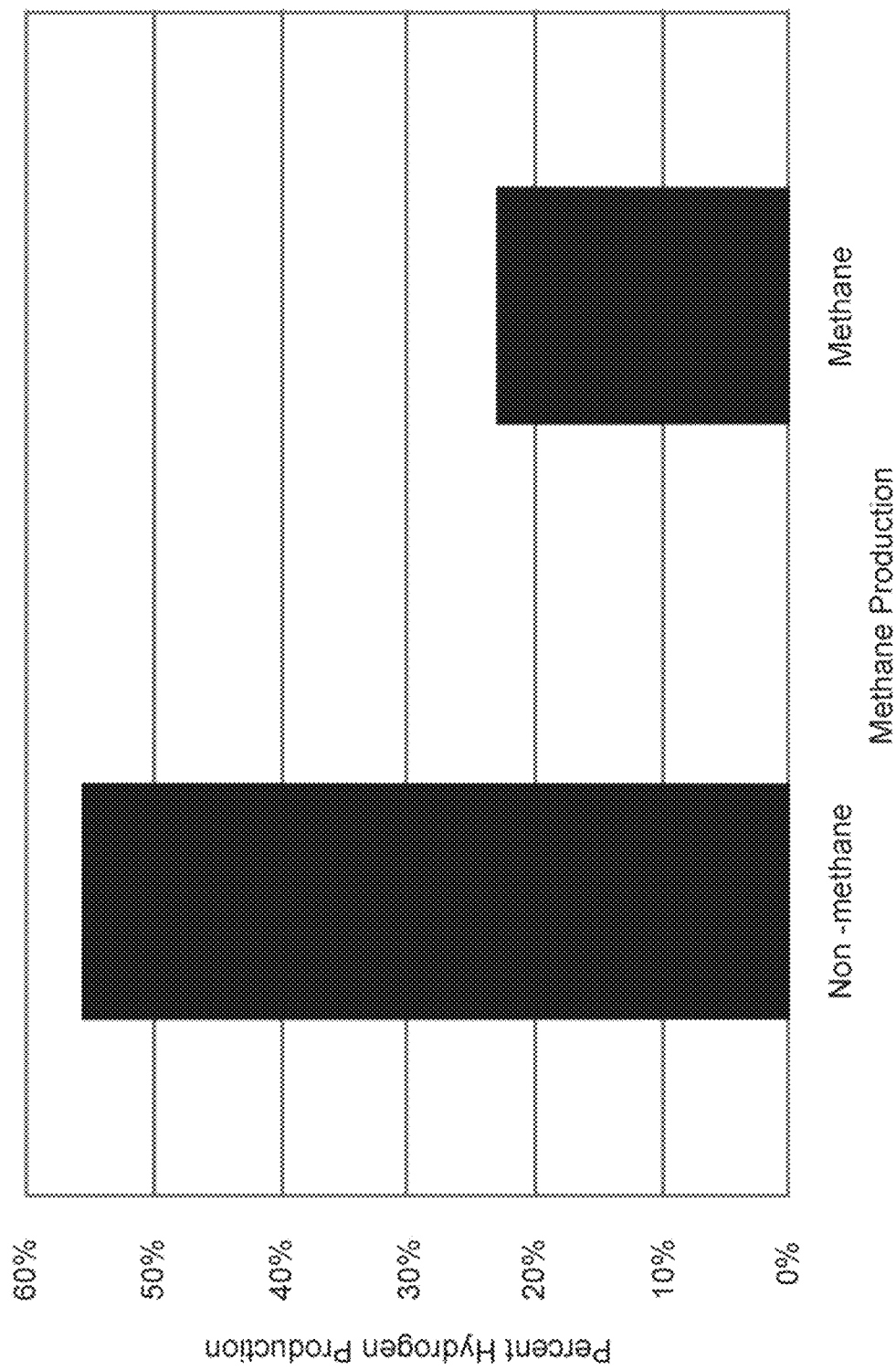
FIG. 6 depicts, in accordance with various embodiments of the present invention, a bar graph showing percent hydrogen production for methane and non-methane producers.

A total of 14,847 breath tests were conducted during this time of which 804 (5.4%) were non-methane, non-hydrogen producers. Of the remaining 14,043 tests (71% female, mean age=47.4±18.3 yrs), 2412 (17.2%) were positive for methane. Irrespective of whether 60 or 90 minutes was used to interpret $H_2$ changes consistent with SIBO, breath tests with methane had a significantly lower breath $H_2$ (see Table 1 and FIG. 6). Examining the change in hydrogen production from baseline, for 60 or 90 minute breath testing interpretation, breath tests with methane also had a reduced rise in hydrogen (Table 1 and FIG. 6 from baseline compared to non-methane breath tests. Furthermore, there were significantly fewer breath tests meeting ≥20 ppm rise of $H_2$ to be considered SIBO in methane producers (23.1%) compared to non-methane subjects (55.7%) (OR=0.20, 95% CI=0.18-0.22) (FIG. 6).

TABLE 1

|  |  | Non-methane | Methane | P-value |
| --- | --- | --- | --- | --- |
| 90 minute breath test (ppm) | AUC of $H_2$ | 85.5 ± 0.6 | 53.7 ± 1.4 | <0.0001 |
|  | Change in $H_2$ | 25.3 ± 0.2 | 10.7 ± 0.4 | <0.0001 |
| 60 minute breath test (ppm) | AUC of $H_2$ | 36.4 ± 0.3 | 28.1 ± 0.8 | <0.0001 |
|  | Change in $H_2$ | 9.6 ± 0.1 | 4.8 ± 0.2 | <0.0001 |

Based on the results, the presence of methane is associated with a significant reduction in hydrogen levels, and dramatically alters the interpretation of hydrogen in breath testing for identification of bacterial overgrowth. Based on these findings, it is imperative to report methane production in clinical reporting and research studies.

Fasting Breath Test for Methane

Excessive methane production can be associated with constipation and bloating. Eradication of methanogen bacteria and decreasing methane production have been shown to improve such symptoms. In a recent consensus meeting at Digestive Disease week 2015, a methane level of ≥10 part per million (ppm) during a standard two-hour breath test was considered the cut off for excessive methane production. Unlike hydrogen gas, patients with excessive methane continue to excrete high levels of methane in the fasting state.

Hence, the accuracy of a single fasting measurement of methane was compared to lactulose breath testing as gold standard. To perform the study, a database of 14847 consecutive lactulose breath tests (71% females) from November 2005 to October 2013 was developed at a tertiary center. A deterministic record linkage was performed to exclude repeated studies of 12183 subjects. In all subjects, after 12 hours of fasting, exhaled methane, hydrogen and carbon dioxide were measured. Patients received lactulose (10 g) and measurements were repeated every 15 minutes for at least 2 hours.

A patient was classified as excessive methane producer if at any point of the study a methane level of ≥10 ppm was detected (gold standard). Test characteristics of various fasting methane levels were compared to gold standard. A sensitivity of >95% and a specificity of >98% was chosen as a priori for test performance. Fisher exact test was used for comparisons. RESULTS: Of 12183 subjects, 1891 (15.5%) were excessive methane producers (68.5% female; mean age 51.9±17.7; age range 3-97 years). Accuracy of various fasting methane levels to identify these patients are shown in Table 1. Although, all single fasting methane measurements performed well, a cut-off of ≥5 ppm was chosen with sensitivity, specificity, positive predictive value and negative predictive value (NPV) of 96.1%, 99.7%, 98.5% and 99.3%, respectively (Table 2 & 3). Performance of the test was not statistically confounded by age or gender. (Table 4)

In the largest database of lactulose breath tests analyzed to date, a single fasting measurement of exhaled methane is highly sensitive and specific to identify excessive methane producers as compared to full lactulose breath testing. This approach can significantly decrease the cost, shorten the study time and omit the bothersome symptoms associated with lactulose intake. Age and gender do not affect the accuracy of fasting methane levels.

TABLE 4

Robust performance of fasting methane level ≥5 ppm based on gender and age with overlapping confidence intervals.

|  | Sensitivity (95% CI) | Specificity (95% CI) |
|---|---|---|
| Females (n = 8647) | 95.8(94.6-96.9) | 99.8(99.6-99.9) |
| Males (n = 3536) | 96.6(94.9-97.9) | 99.7(99.4-99.8) |
| Age <18 (n = 543) | 90.7(77.9-97.4) | 99.8(98.9-100) |
| Age 18-65 (n = 8778) | 96.2(95-97.2) | 99.7(99.6-99.8) |
| Age ≥65 (n = 2682) | 96.2(94.3-97.6) | 99.7(99.4-99.9) |

Methane Production and Age

There is mounting clinical evidence that excessive methane production can be associated with constipation and bloating. Eradication of methanogens and decreasing methane production have been shown to improve such symptoms. In human study, methanogenic colonization of the intestinal tract increases throughout childhood but reaches a peak in adolescence. However, large-scale studies are lacking to explore the demographic determinants of methane production.

A database consisting of 14,847 consecutive lactulose breath tests, performed between November 2005 and October 2013 in a single institution was developed. Using date of birth, medical record number, first and last name; a deterministic record linkage was performed to exclude repeated studies. Hence, a total of 12,183 breath tests were classified into six categories: 1—Normal: Methane levels <3 parts per million (ppm) and hydrogen levels <20 ppm within the first 90 minutes. 2—Positive hydrogen: Methane levels <3 ppm and hydrogen levels ≥20 ppm within 90 minutes. 3—Positive methane: Methane levels ppm and hydrogen <20 ppm.

TABLE 2

Test characteristics of various single fasting methane levels as compared to the gold standard test.

| Fasting methane level (ppm) | Sensitivity (95% CI) | Specificity (95% CI) | PPV (95% CI) | NPV (95% CI) | +LR | −LR |
|---|---|---|---|---|---|---|
| ≥10 | 86.4 (84.8-87.9) | 100* | 100 (99.8-100) | 97.6 (97.3-97.8) | Not applicable* | 0.14 |
| ≥9 | 88.8 (87.3-90.2) | 100 (99.9-100) | 99.9 (99.6-100) | 98 (97.7-98.2) | 4569 | 0.11 |
| ≥8 | 90.7 (89.3-92) | 99.9 (99.9-100) | 99.7 (99.2-99.9) | 98.3 (98.1-98.6) | 1557 | 0.09 |
| ≥7 | 93 (91.8-94.1) | 99.9 (99.8-99.9) | 99.3 (98.7-99.6) | 98.7 (98.5-98.9) | 736 | 0.07 |
| ≥6 | 94.6 (93.4-95.5) | 99.7(99.6-99.8) | 99.1 (98.5-99.5) | 99 (98.8-99.2) | 572 | 0.05 |
| ≥5 | 96.1 (95.1-96.9) | 99.7(99.6-99.8) | 98.5(97.8-99.0) | 99.3(99.1-99.4) | 353 | 0.04 |
| ≥4 | 97.3 (96.4-97.9) | 99.6 (99.4-99.7) | 97.7 (96.9-98.3) | 99.5 (99.3-99.6) | 227 | 0.03 |
| ≥3 | 98.8 (98.2-99.3) | 99.3 (99.1-99.4) | 96 (95.1-96.9) | 99.8 (99.7-99.9) | 132 | 0.01 |

*Single methane level equal or greater than 10 ppm fulfills the gold standard test for methane positivity. CI: Confidence interval; NPV: Negative predictive value; PPV: Positive predictive value.

TABLE 3

2 × 2 contingency table for fasting methane level ≥5 ppm as compared with gold standard test

|  | Gold Standard (Full breath test) | |
|---|---|---|
|  | Methane producer | Non-Methane producer |
| Fasting methane ≥5 ppm | 1817 | 28 |
| Fasting methane <5 ppm | 74 | 10264 |
|  | 1891 | 10338 |

4—Hydrogen and methane positive: Methane levels ppm and hydrogen levels ≥20 ppm within 90 minutes. 5—Flatliners: Methane <3 ppm and hydrogen ≤3 ppm with variation ≤1 ppm within 120 minutes. 6—Equivocal: Hydrogen levels above 20 ppm at baseline prior to ingestion of lactulose and methane $<^3$ ppm.

Figure 7:
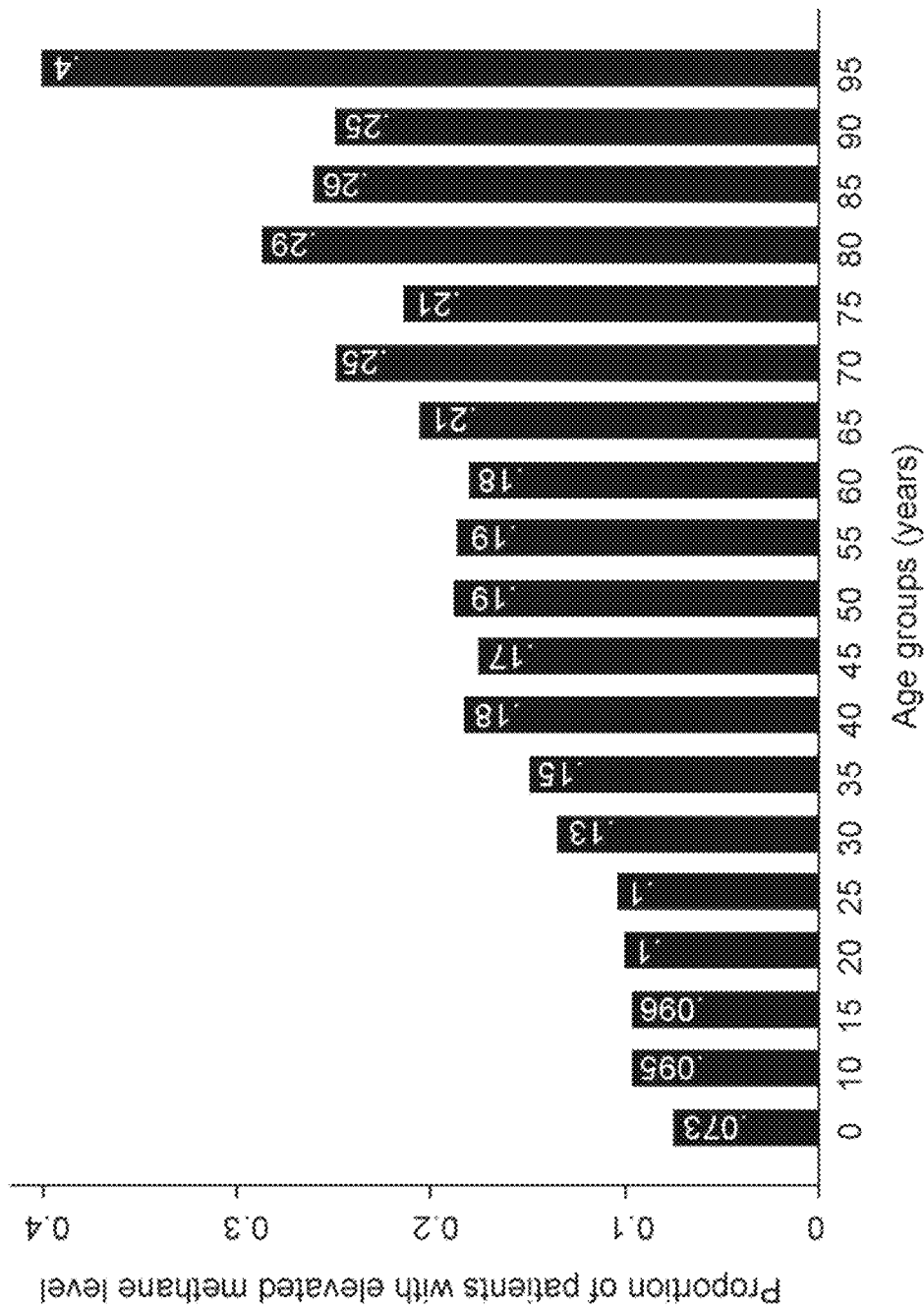
FIG. 7 depicts, in accordance with various embodiments of the present invention, a bar graph showing population of patients with elevated methane levels by age.

Of the 14.847 breath test subjects, most were females (71%). Average age at the time of breath test was 46.9±18.3 years (range 2-101). The proportions of each category of breath test result are represented in Table 1. Male subjects were significantly more likely to produce excessive amounts of methane (18.21% vs. 16.07%, p<0.01); however, no other significant differences existed between the two genders. Regardless of gender and hydrogen production, those producing abnormally high amounts of methane were significantly older than non-methane gas producers with a mean age of 52.3 years and an age difference of 5.8 years (p<0.01). The equivocal group was the youngest group with a mean age of 34.8 years (p<0.01). The prevalence of methane production appeared to increase with age, as shown in FIG. 7.

In the largest database of lactulose breath tests analyzed to date, the prevalence of methane gas on breath test increases by more than five-fold with age, with the oldest age group having the highest prevalence of methane producers. This finding may explain why age is a known risk factor for constipation. Finally, with a difference of approximately 2%, males were slightly but significantly more likely than females to be methane producers, the clinical significance of which has yet to be determined.

TABLE 5

Proportion of breath test categories

|  | Mean age ± SD | Female | Male | p-value | Overall |
|---|---|---|---|---|---|
| Normal Breath Test | 46.82 ± 18.37 | 31.10% | 30.51% | 0.261 | 30.90% |
| Positive $H_2$ | 45.45 ± 18.15 | 48.77% | 47.85% | 0.312 | 48.50% |
| Positive $CH_4$ | 52.33 ± 17.55 | 12.22% | 13.83% | 0.016* | 12.69% |
| Positive $H_2$ and $CH_4$ | 49.95 ± 18.46 | 3.85% | 4.38% | 0.174 | 4.01% |
| Flatliner | 47.64 ± 17.43 | 3.46% | 2.91% | 0.126 | 3.30% |
| Equivocal | 34.84 ± 16.63 | 0.60% | 0.51% | 0.541 | 0.57% |

Example: Breath Gas System with Manifold

In some examples, systems and methods have been developed to determine concentrations of multiple breath gases using multiple sensors with a single device and one breath sample from a patient. For instance, a reliable determination of whether a patient has SIBO may require testing each of $CO_2$, $H_2$, $H_2S$, and $CH_4$ gases for the reasons disclosed herein. Accordingly, measuring each of these gasses with a single exhaled breath from a patient would be the most efficient and accurate way to determine these concentrations and apply a diagnostic algorithm.

However, developing a system that can test multiple gasses using multiple sensors is challenging for a variety of reasons. For instance, exhaled patient breath is typically completely saturated with water and contains 100% relative humidity. Thus, if this breath gas is passed through a room temperature testing device, at least some of the water will condense on the surfaces of the device it contacts. This is an issue for multiple reasons, including that some sensors used to test gas concentrations are sensitive to humidity which would bias the readings. Additionally, condensation could damage certain types of sensors.

Therefore, to remove humidity prior to passing the exhaled air over sensors to ensure accurate readings, some previous devices have utilized desiccants or other absorbents (e.g. a bed of activated aluminum to first remove moisture). However, using absorbent materials is not advantageous for a multitude of reasons, including: (1) the absorbent material would need to be regularly replaced, (2) the amount of moisture absorbed one each breath would change as the absorbents become saturated which creates calibration issues—especially gasses with low concentrations like hydrogen sulfide, and (3) there needs to be extra volume in the manifold (and of exhaled gasses) so that there is space to first pass the exhaled gas over the absorbent material.

Furthermore, absorbent materials may actually absorb certain gasses. For instance, $H_2S$ is known to be absorbed by certain sorbent materials, including desiccants. Therefore, utilizing desiccants is not advantageous, especially for a system that tests for multiple gases including $H_2S$.

Accordingly, systems and methods have been developed to test for multiple gases in exhaled breath without using absorbent technology. In some examples, this includes a system that uses a manifold to maintain the temperature of the exhaled breath gases as they flow through the channels of the manifold. In this example, the gasses are heated to at least body temperature or higher to avoid condensation of the moisture in the exhaled breath. This prevents the requirement of using desiccants or other absorbent technologies. Furthermore, some electrochemical sensors are more sensitive at higher temperatures, and accordingly will require a shorter time to acquire an accurate reading when heated to certain temperature ranges (e.g. 40 degrees Celsius and higher) which is advantageous for the reasons described herein.

Furthermore, the device must maintain the breath gasses at a consistent temperature and flow rate while testing them in the device to ensure that accurate measurements are taken once the sensors are calibrated. This is particular important for gasses like $H_2S$, which have relatively low concentration (e.g. 9-10 ppb) compared to the other gasses present in exhaled breath. Furthermore, because the total volume of gas exhaled by a patient for a sample is relatively small, it can be challenging to maintain a consistent temperature and flow rate if there are multiple gas sensors required (e.g. three or four gas sensors as disclosed herein), as there will be a longer gas flow path required so that the gas contacts the sensor probes for each of the sensors.

In some examples, a metal manifold with high thermal conductivity may be utilized to maintain the temperature of gas passing through the channels within a narrow range, that would be controlled using temperature control elements as disclosed herein (e.g. PCB's with thermistors and heating elements). Furthermore, if a single channel is utilized that introduce the sensors in serial fashion rather than splitting the gas flow path into parallel channels for each sensor, the total volume required will be less, allowing sufficient gas to pass over the sensors to record an accurate reading at the disclosed temperature range.

In some examples, the channel could be split into two channels with sensors mounted on the top and bottom of the channels so that multiple sensors (e.g. two, three, four, etc.) could be introduced into the channel within a short distance. However, the inventors found that in some cases splitting the gas flow path into parallel channels required too much volume of gas in some configurations.

Additionally, in some examples, a relatively larger and accurate methane sensor may be utilized that is separate from the manifold and connected to the manifold channel with a pipe or other gas flow path as the methane sensor may not require constant flow rate and temperature.

Because a constant flow rate is required, the faster the sensors acquire an accurate reading the less volume of gas that is required. Accordingly, in some examples, baffles, bumps, or other partial obstructions are utilized to introduce turbulence into the flow adjacent to each or some of the sensors measuring probes. This provides an increased gas exchange time which then requires less overall volume of exhaled air.

Accordingly, these features together allow a single exhalation of air or a smaller volume of air to be introduced into a system that measures at least $CO_2$, $H_2$, $H_2S$, and $CH_4$ without using desiccants and acquiring a stable and accurate readings. This will allow the system to accurately assess the SIBO status of a patient and other potentially indications.

Detection of all four gasses may be critical to determining a full picture of whether a patient has SIBO, and diagnosing related symptoms. For instance, as described in International Patent Publication WO 2018/154937 published on Aug. 30, 2018, titled "MEASUREMENT OF HYDROGEN SULFIDE DURING BREATH TESTING," the content of which is incorporated herein by reference in its entirety, some subjects who are characterized as having normal $H_2$ and $CH_4$ levels tested posited for $H_2S$. The study referenced in the application is discussed in more detail in the examples below. Accordingly, testing for all three gasses can be critical to determine a full diagnostic picture of a patient, and this especially includes testing for $H_2S$. As discussed herein, prior art systems do not have these same features and advantages.

Figure 8:
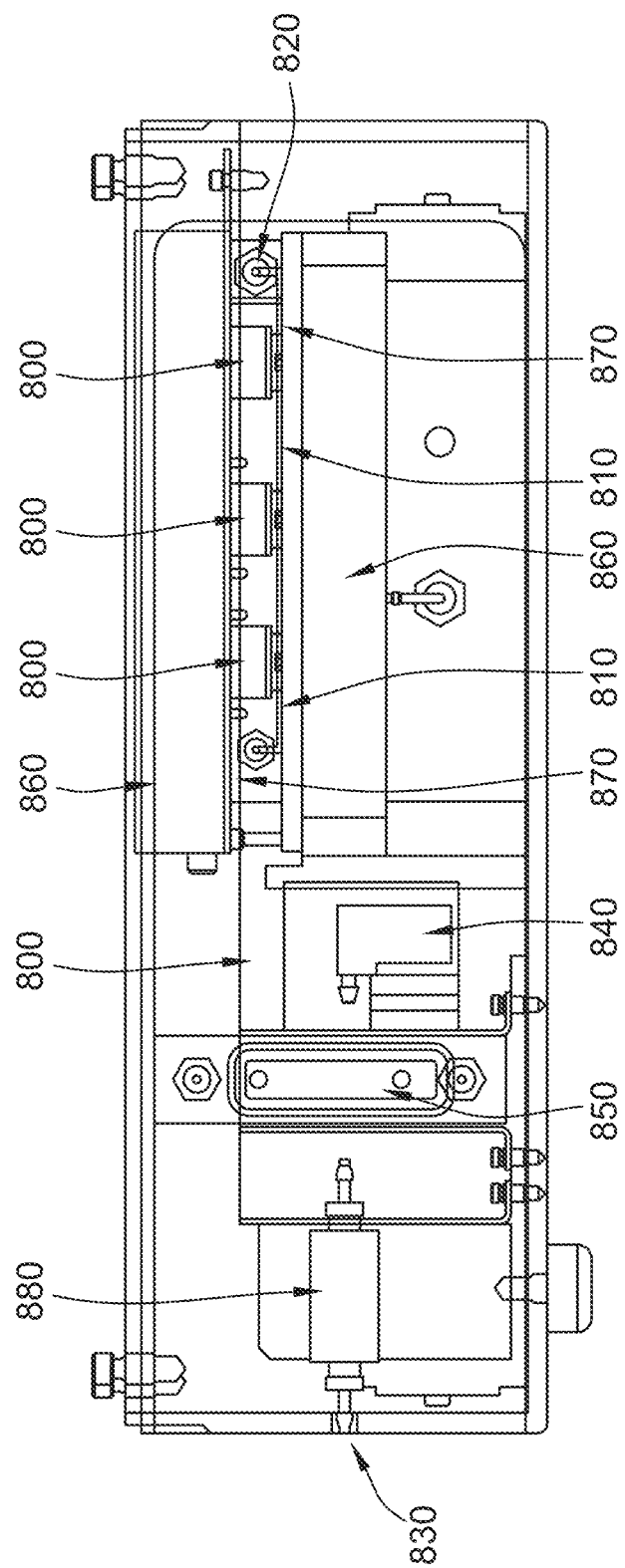
FIG. 8 depicts, in accordance with various embodiments of the present invention, a side view of a gas detection device.

FIG. 8 is an example of a system used to test breath gases exhaled from a patient. The system may include a gas inlet 820 that receives gases exhaled from the patient. The gas inlet may be any suitable valve or other port. In some examples, the inlet 820 may be connected to various breath collection devices as disclosed herein or may be connected to a balloon or bag with previously collected gasses.

The inlet 820 may be in gaseous communication with a gas flow path 810 through a manifold 860. A manifold 860 may be any suitable thermally conductive material with a gas flow path 810 constructed through the manifold 860. For instance, the manifold 860 may be made of metal and may have channels, pipes or paths constructed for the gas to flow. In some examples, the manifold 860 may be constructed from stainless steel. In some examples, it may be coated with copper. In other examples, the manifold 860 may be pipes or other suitable mechanical components that provide for a gas flow path 810. In some examples, the manifold 860 may be manufactured from thermally resistive material or insulator and the thermal regulatory elements may maintain the gas temperature directly without heating the manifold material.

The system may include a thermal regulation element 870 that includes temperature sensors and heating elements. In some examples, the thermal regulation element 870 may be a printed circuit board that includes thermistors for measuring the temperature of the manifold 860 and/or gas flow path 810 and various heating elements (e.g. resistive) for heating the manifold and/or air flow path.

In some examples, the heating elements may include traces printed on a printed circuit board in place of separate coils. This will allow a more compact construction and cheaper manufacturing costs. Because the temperature ranges required are below the melting point of the printed circuit board, and generally below the level at which they would cause damage, traces on the printed circuit board themselves could advantageously be used.

In some examples, thermal regulation element 870 may include a plurality of temperature sensors and heating elements that separately regulate different portions or zones of the manifold 860. For instance, there may be separate regulatory combination (temperature sensor and heating element) for zones that may include: (1) top and bottom of a manifold, (2) zones next to each of the sensors, (3) front and back halves of the manifold, (4) pipes, flow paths, or channels between sensors, or other suitable distributions based on the temperature tolerance of the sensors and the sensitivity of the regulation system. For instance, the thermistor and heating element could be positioned in the center or in a portion of each of the zones to optimally heat the zone.

These different thermal regulatory elements 870 may be contained on separately printed circuit boards, the same printed circuit boards or utilize other suitable control systems and connections. In some examples, the thermal regulatory elements 870 may be configured to sensor the gas temperature in the gas flow path 810 and heat either the manifold 860 or directly heat the gasses inside the gas flow path 810.

The elements may be configured to regulate the temperature using a closed loop feedback system. This may include regulating the temperature to ensure it is higher than body temperature (37 degrees Celsius) to prevent condensation from the breath forming on the components and wearing them or making the gas concentration readings inaccurate. In some examples, the system may use a threshold of 40 degrees Celsius (minimum temperature) or other suitable threshold such as 38 degrees, Celsius, 39 degrees Celsius or 37 degrees Celsius as minimum temperatures. In some examples, the thermal regulation element 870 may keep the temperature of the manifold and/or gasses in the passages within a range of 1 degree Celsius, 2 degrees Celsius or other suitable ranges (e.g. 38-40 degrees Celsius, or 40-42 degrees Celsius).

The gas flow path 810 may include various sensors 800 to sense various gases including, for instance, methane ($CH_4$), hydrogen ($H_2$), hydrogen sulfide ($H_2S$), and/or carbon dioxide ($CO_2$). The sensors may be electrochemical sensors, laser based sensors or other suitable sensors. In some examples, the hydrogen, hydrogen sulfide, and carbon dioxide sensors may be electrochemical based sensors and the methane sensor may be a laser based sensor placed at the end or outside of the manifold 860.

The sensors 800 may be integrated into the manifold 860 or otherwise posited and constructed in the system to allow a sensor probe 800 of the sensors to detect the gasses flowing through the gas flow path 810. In some examples, a linear or approximately linear gas flow path 810 may include a line of sensors 800 that test the gas in a serial fashion as the gas passes through the gas flow path 810. In other examples, the gas flow path 810 may split into separate channels to allow the sensors 800 to test the gas in parallel or other combinations of serial and parallel.

In some examples, a gas flow path 810 may have sensors 800 that enter the flow path only from the top or bottom. In other examples, sensors 800 may be mounted on both the top and bottom of the gas flow path 810, and therefore a shorter linear or parallel flow path 810 may be required for all four or three sensor probes (or other number of sensor probes).

In some examples, the system may include a pump 840, for instance a diaphragm pump, and a flow meter 850 to pump the exhaled breath through the gas flow path 810 at a constant rate. This may be important, because some sensors 800 may require a constant, calibrated flow rate to record an accurate gas concentration reading.

Additionally, the system may include a gas exhaust 830 through which the gas in the gas flow path would exit the system. In some examples, after a reading has been performed, the system may activate a pump 840 to purge the gas flow path 810 from excess exhaled gases from a patient so that ambient air is withdrawn through the gas inlet 820 and expelled through the gas exhaust 830. In some examples, this may automatically occur after each reading for a predetermined amount of time, for instance, a few seconds, 20 seconds, 30 seconds, 1 minute, or other suitable time frames.

Figure 9:
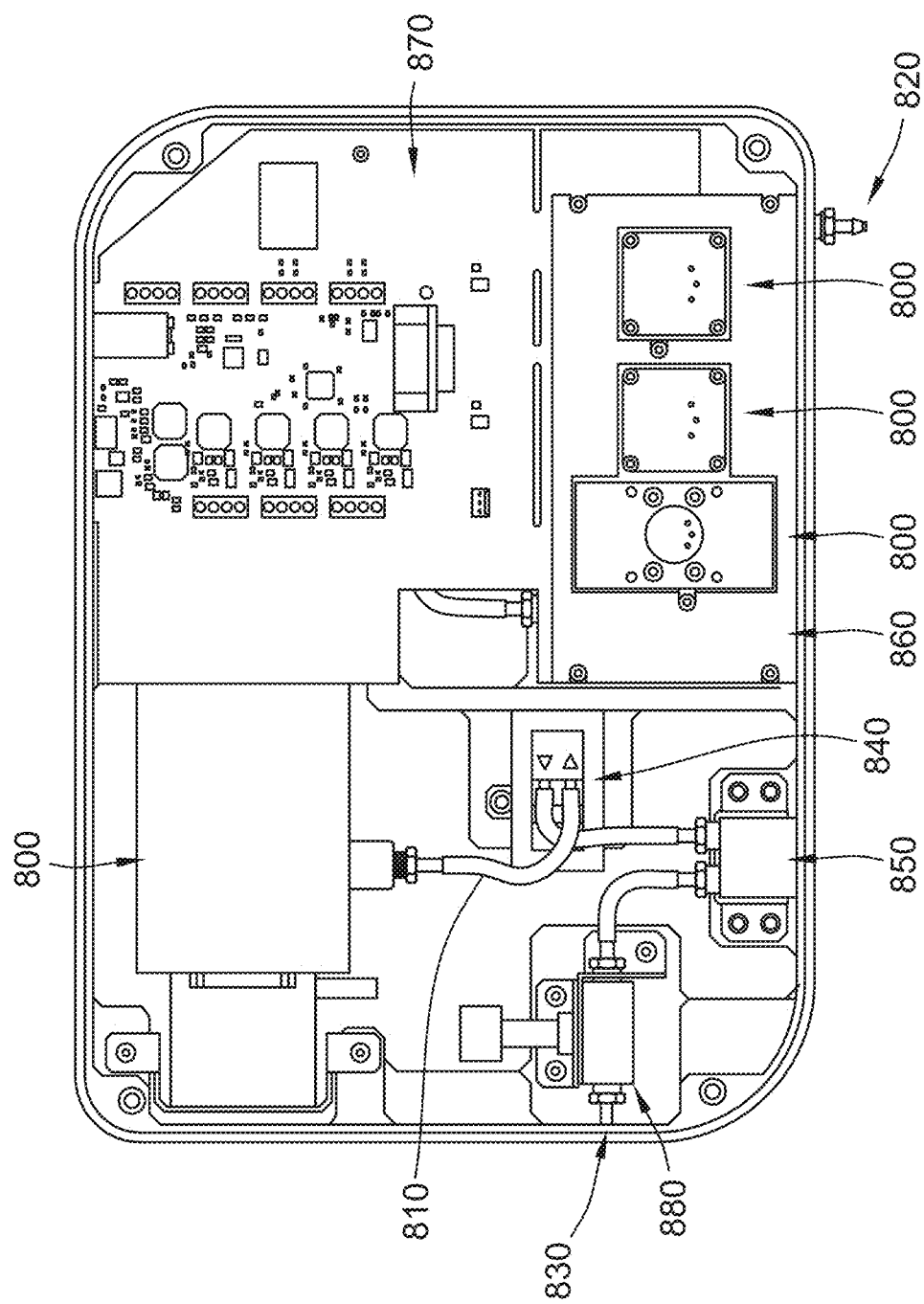
FIG. 9 depicts, in accordance with various embodiments of the present invention, a top view of a gas detection device.

FIG. 9 illustrates an example top view of the system. In this example, the thermal regulatory element 870 includes a printed circuit board that is adjacent to the manifold 860. In this example, the printed circuit board may include various thermistors or other temperature sensors and heating elements spaced at varying positions to regulate various zones of the manifold 860. As illustrated, portions of the gas flow path 810 may include pipes and other portions may be channels in a manifold 860 or the manifold 860 may itself be constructed from pipes.

Figure 10:
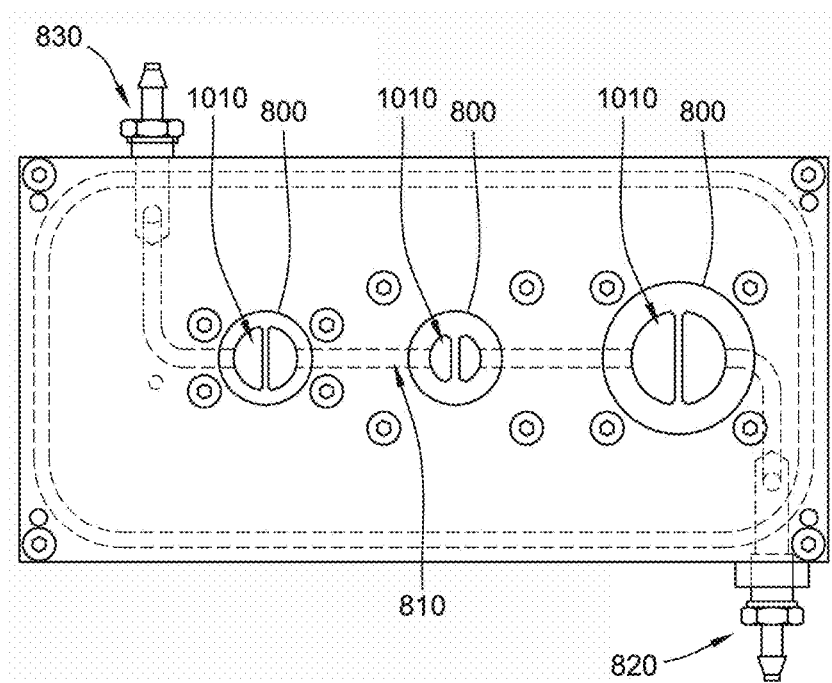
FIG. 10 depicts, in accordance with various embodiments of the present invention, a top view of a gas detection device.

FIG. 10 illustrates a top or bottom view of an example of a breath gas sensing system according to the present disclosure. In this example, then gas flow path is illustrated as a channel in a manifold 860, and the manifold 860 is illustrated as a block of metal or other thermally conductive or resistive material. In this example, the sensors 800 are arranged in serial positions along the gas flow path 810 and have a baffle or partial obstruction 1010 adjacent to each sensor 800 along the flow path 810. In other examples, the gas flow path 810 may be split into separate channels or gas flow paths 810 that each of different sensors 800 with probes that access the gas flow path 810.

The baffle or partial obstruction 1010 may be a bump, depression, or other shape or configuration that directs the gas towards a sensor 800 or sensor probe and in some embodiments introduces turbulence into the gas flow. In other embodiments, a constant flow rate will still be maintained without creating turbulence, but the main flow of the gasses will be diverted towards the sensor 800 using the baffle 1010.

Figure 11:
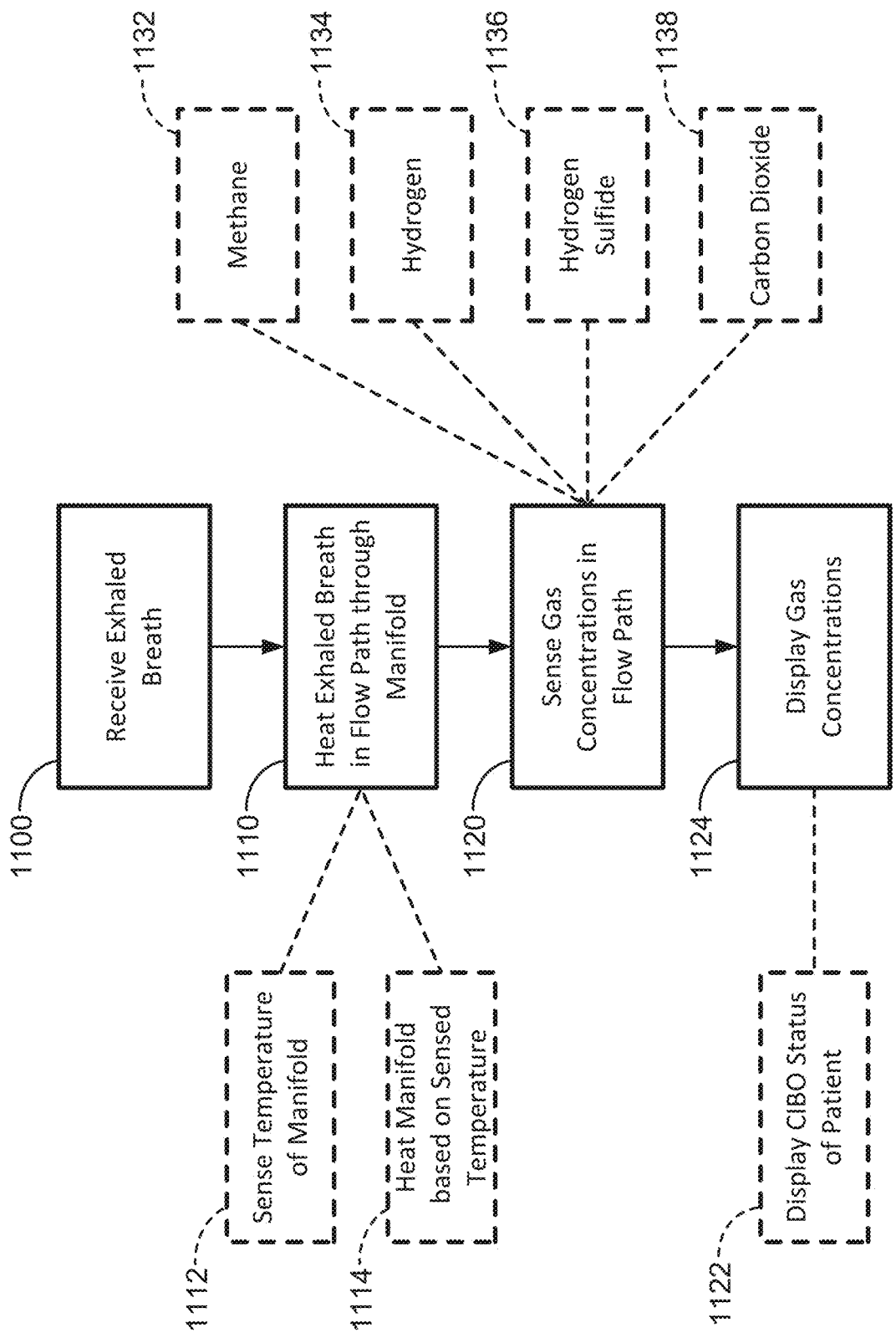
FIG. 11 depicts, in accordance with various embodiments of the present invention, a flow chart depicting a method of testing breath gases.

FIG. 11 illustrates a flow chart of an example of a method for testing the breath of a patient for various concentrations of gases. As disclosed herein, this may be performed for a variety of reasons or outcomes/outputs, including to diagnose the patient with certain diseases based partially on the gas concentrations detected including SIBO.

First, the system may receive exhaled breath from the patient 1100. This may be from a breath collector such as a nozzle, bag, or other suitable device. Next, the breath gas will be heated in a flow path through a manifold 1110. This may be performed with a variety of thermal regulation systems and at various positions along the flow path. For instance, the system may heat the exhaled breath gas prior to entering certain sensors or all sensors. In one example, the breath gas may be initially heated and then passed over the sensors.

In other examples, the system may heat the breath gases at various points along its travel through the gas flow path. As disclosed herein, various systems may be utilized to heat the components forming the gas flow path (e.g. directly heating the manifold) or the gas itself may be directly heated. For instance, a regulation system may sense the temperature of the manifold 1112, for instance using a thermistor in contact with the manifold 860 or an infrared temperature sensor or other suitable temperature sensors.

This data then may be utilized to implement a closed feedback loop with various heating elements which may include resistive heaters to heat the components of the system to a suitable temperature based on feedback from the temperature sensor 1114 (usually above body temperature to avoid condensation, unless the system first includes a dehumidifier, in which case the temperature may be lower).

Next, the system may sense gas concentrations along the flow path 1120 with various sensors. This may include methane 1132, hydrogen 1134, hydrogen sulfide 1136, carbon dioxide 1138, or other relevant gases depending on the application for monitoring or diagnosing the patient. Then, these gas concentrations may be displayed 1124, stored, transmitted, or may be further utilized to determine and display a disease status of the patient—for instance whether the patient has SIBO 1122 or a likelihood the patient has SIBO. In some examples, the methane 1132 sensor 800 may be connected separate from the manifold, and instead may be connected with pipes to the manifold channel. This may be the case where the methane sensor is a larger and more accurate sensor and thus would not easily fit in the manifold and would not require the consistent flow rate and temperature to accurately measure the methane concentration.

In some examples, the system may determine a hydrogen and methane concentration of gasses exhaled by the patient, determine a methane calibrated change of the hydrogen level, and then output an indication of whether the patient has SIBO based on the detected hydrogen level. Additionally, the system may determine or diagnose other disease based on the breath gases detected by the system.

Example: The Importance of Hydrogen Sulfide in Clinical Breath Testing: Validation of a Novel 4-Gas Breath Testing Device As discussed above, detection of all four gasses is very important to providing an accurate determination of whether a patient has SIBO, and diagnosing related symptoms. For instance, in a study evaluating an example of a device that tested $CO_2$, $H_2$, $H_2S$, and $CH_4$ breath gas levels in patients using a manifold heating system as disclosed herein, it was determined that testing for all four gasses (and especially $H_2S$), was vitally important to evaluating the results.

For instance, some subjects who are characterized as having normal $H_2$ and $CH_4$ levels tested posited for $H_2S$. Furthermore, because $H_2$ can be converted into $CH_4$ and $H_2S$, testing all four gasses (including calibrating with $CO_2$) is very important to accurately correlating SIBO and its systems to these gas levels, as testing any subset will likely not accurate assess the diagnosis and severity of indications for a given patient, given the interaction between the gasses.

Finally, $H_2S$ was found to be associated with certain diarrhea phenotypes. Accordingly, testing for all four gasses can be critical to determine a full diagnostic picture of a patient, and this especially includes testing for $H_2S$. As discussed herein, prior art systems do not have these same features and advantages. Following is a summary of the study and its findings.

Overview

Hydrogen ($H_2$) breath testing has been used to evaluate small intestinal bacterial overgrowth (SIBO) during the work-up of diarrhea. However, $H_2$ levels are not linked to diarrhea severity, whereas methane ($CH_4$) is associated with constipation. Both $CH_4$-producing and hydrogen sulfide ($H_2S$)-producing organisms consume $H_2$, but $H_2S$ cannot be studied using conventional breath testing systems and methods. Therefore, a novel 4-gas device ($H_2$, $CH_4$, $H_2S$, and $CO_2$) was assessed to determine whether this provides a more comprehensive breath test.

Consecutive subjects referred for breath testing were eligible. Subjects provided a baseline breath sample, ingested 10 g lactulose, then provided additional samples every 15 minutes for 120 minutes. Subjects completed a symptom questionnaire. Samples were analyzed for $H_2$ and $CH_4$ using a conventional instrument followed by the 4-gas device. Results from both instruments were compared, and symptoms were correlated with gas patterns from the 4-gas device. Gas interactions were also assessed.

Referring to FIG. 14, 298 subjects completed the study. Measurements from both instruments correlated strongly ($H_2$: R=0.90; $CH_4$: R=0.97). Using the 4-gas device, a positivity threshold of >1.2 ppm was determined for $H_2S$ and associated with diarrhea. 56.9% of subjects with $H_2S>1.2$ ppm reported severe, as compared to moderate or mild, diarrhea (P=0.01). The additional presence of $CH_4$, $H_2S$, or both, had significant impacts on $H_2$ levels and diarrhea severity. $CH_4$ dominated the effects by reducing diarrhea (P=0.02).

Background of Study

Breath testing has been used clinically for over 30 years in the assessment of small intestinal bacterial overgrowth (SIBO), most notably in the work-up of unexplained diarrhea [1]. The technique was originally based on the principle that gases produced by intestinal microbes during the fermentation process are unique and not produced by the human host. However, the physiologic consequences of these gases in terms of human disease have only recently begun to be understood.

In current breath testing techniques, patients ingest a fermentable substrate after fasting for a period of time. Breath samples are obtained at baseline and then at regular intervals over the next several hours, and are tested for levels of hydrogen ($H_2$) as well as carbon dioxide ($CO_2$). While $H_2$ is only produced by gut microbes, $CO_2$ is produced by human cells and is measured to correct the breath sample to alveolar concentrations. Based on the recent North American Consensus on breath testing [2], a rise of $H_2$ by more than 20 parts per million (ppm) within 90 minutes of administration of a fermentable substrate is suggestive of SIBO. Although this pattern of $H_2$ production appears predictive of response to antibiotics [3], studies have failed to correlate $H_2$ levels with degree of diarrhea or other symptoms for which the test is ordered. In contrast, $CH_4$ has gained a significant amount of attention in that it appears to be both predictive of, and proportional to the severity of, constipation.

In the intestinal tract, gas production and utilization is a complex process of interactions between various microbes. It is now known that $H_2$ is produced in large quantities by fermenting bacteria, but is also a substrate for the production of other gases [6]. For example, 4 molecules of $H_2$ are used by methanogenic archaea to produce 1 molecule of $CH_4$ gas [6]. In addition, there are at least 2 other disposition pathways for $H_2$: acetogenesis by homo-acetogens and hydrogen sulfide ($H_2S$) production by sulfate-reducing bacteria [6]. Given that there is a complex interplay between these gases, it is impossible to fully understand the clinical breath test without measuring all of these microbially-produced gases.

In this study, a novel device capable of measuring all 4 gases ($H_2$, $CH_4$, $H_2S$, and $CO_2$) during clinical breath testing was tested. This was performed to determine if measurement of $H_2S$ levels enables the prediction of clinical symptoms and allows a better understanding of the competing interactions between $H_2$, $CH_4$, and $H_2S$, thus providing a more comprehensive breath test, among other aspects.

Methods

For the study, subjects were required to undergo a 24-hour preparation period immediately prior to the study, avoiding consumption of fruits, vegetables, dairy products, and beans for the first 12 hours, and then fasting for the second 12 hours. Subjects were not allowed to smoke or exercise immediately prior to, or during, the test. A baseline exhaled breath sample was collected. Subjects then consumed 10 g lactulose dissolved in 200 mL water. Subsequent breath samples were collected every 15 minutes over the remaining 120 minutes. Samples were analyzed immediately, with 20 cc of the sample being analyzed using a QuinTron Breath-Tracker™ (QuinTron Instruments Co., Milwaukee, WI) and the remainder of the sample being analyzed using a new 4-gas detection device. Both devices analyzed breath components via gas chromatography and corrected outputs to a $CO_2$ concentration of 5.50% based on the alveolar level.

The new 4-gas detection device required calibration prior to use. Following a brief warm-up period, the machine was calibrated first using ambient air and then a mixture of ambient air and calibration gas (QuinTron Instruments Co., Milwaukee, WI). A total of 3 runs were performed for each calibration set. The machine remained calibrated for 16 hours. To analyze samples, the bags were attached to the machine via an inlet, the stopcock was opened, and the machine ran for 120 seconds with real-time output via a computer interface. A 30-second purge cycle followed each run. The 4-gas device simultaneously measured all gases ($H_2$, $CH_4$, $H_2S$, and $CO_2$) in ppm with an accuracy of ±0.2 ppm.

During the breath test, subjects were asked to complete an in-depth questionnaire regarding their medical history, demographics, and bowel symptoms. Symptom severity was measured using a 0-100 mm visual analogue scale (VAS).

For both instruments (conventional and the novel 4-gas device), the determination of a positive breath test was based on the recent North American Consensus [2]. For $H_2$, a test was considered positive if there was a rise of ≥20 ppm from baseline at or before 90 minutes. For $CH_4$, a level ≥10 ppm at any point during the breath test was considered positive. Since a positive threshold for breath $H_2S$ had not been previously defined, one was determined based on the results of this study.

Data Processing

In order to validate the accuracy of the novel four gas detection device, all measurements of $H_2$ and $CH_4$ obtained were compared to those from the conventional QuinTron instrument to assure the new device was accurately measuring those gases. In addition, the level of agreement for positive $H_2$ and $CH_4$ breath tests between the instruments was determined. Subsequently, $H_2S$ levels were evaluated across the study to determine the range of values and meaningfulness of this additional gas. Gas profiles were then compared to symptom severity among study subjects. Finally, given that $H_2$ is a substrate for the production of both $CH_4$ and $H_2S$, the interplay between these three gases was evaluated to further understand the scientific and clinical value of adding $H_2S$ to clinical breath testing.

For comparison of the two breath testing techniques, a Spearman correlation was performed. To assess the level of agreement for positive $H_2$ and $CH_4$ breath tests between the QuinTron instrument and the new device, Cohen's kappa was used. However, since the new instrument had an error level of ±0.2 ppm for these gases and QuinTron reports an error level of ±2 ppm (10-fold less sensitive), factored this error level was factored into the analysis of positive breath tests for the QuinTron instrument. Descriptive analyses were conducted to examine the distribution of population characteristics, diagnosis records, and symptom severity via VAS. Spearman correlation between symptom VAS scores were evaluated.

All 20 symptoms were grouped into 3 categories: foregut symptoms, irritable bowel syndrome (IBS) symptoms, and diarrhea-predominant IBS (IBS-D) symptoms. It should be noted that IBS-D symptoms also fall within the IBS category. Foregut symptoms include belching, hoarseness, clearing the throat, difficulty swallowing, coughing after eating, breathing difficulties, annoying cough, sensation of something sticking in the throat, and heartburn or chest pain. IBS symptoms include bloating, excess gas, incomplete evacuation, abdominal pain, constipation, diarrhea, urgency with bowel movement, discharge of mucus from the rectum, and straining during bowel movement. Bloating, excess gas, abdominal pain, diarrhea, urgency with bowel movement, and discharge of mucus from the rectum were categorized as IBS-D symptoms.

To determine if $H_2S$ production was an indicator of IBS-D/diarrhea-related symptoms, first generalized linear regression models were fit to test the association, and then Wilcoxon was used to evaluate thresholds of $H_2S$ positivity using a derived variable. The optimal discriminating level was determined to be ≥1.2 ppm which was used to define a positive test for $H_2S$. Combinations of IBS-D symptoms were further evaluated using combinatorial analysis, where n is number of IBS-D symptoms:

$$\text{Possibilities} = nC1 + nC2 + \ldots + nCn$$

Second, to visualize gas patterns across time, a local regression (LOESS) was fit with $H_2$, $CH_4$, and $H_2S$ levels against time points individually and stratified by the number of consuming gases. Subjects who were neither $CH_4$ nor $H_2S$ positive were categorized as "No Consuming Gases Positive", subjects who were positive for either $CH_4$ or $H_2S$ but not both were categorized as "One Consuming Gas Positive", and subjects who were positive for both $CH_4$ and $H_2S$ were categorized as "Two Consuming Gases Positive". To further evaluate the interaction of consuming gases, cumulative $H_2$ production between consuming gas groups was compared using an ANOVA model, followed by Tukey post-hoc test.

Statistical analyses were performed using SAS (Statistical Analysis System) version 9.4 (SAS Institute Inc., Cary, NC) and R version 3.4.3 software (R Foundation for Statistical Computing, Vienna, Austria).

Results

A total of 300 subjects were recruited for this study. Of these, two did not complete the questionnaire fully and were excluded, such that 298 subjects were included in the final analysis. Of these 298 subjects, 196 were female (66%). The average age was 49 years (range 19-88 years) and the average BMI was 24.7 kg/m2 (range 15.7-54.1 kg/m2). Of the 298 subjects, 40% were diagnosed with IBS, 44% with constipation, 4% with ulcerative colitis, 7% with Crohn's disease, and 6% had a history of intestinal infection. In addition, 18% had undergone a breath test at our clinic within the last year, 30% had experienced weight loss, and 7% reported blood in the stool. The population characteristics and questionnaire results are presented in FIG. 12.

The severities of 20 symptoms were measured by VAS. Of these, 14 were normally distributed. The remaining 6 were heavily left-skewed as they were uncommon, and included discharge of mucus from the rectum; difficulty swallowing food, liquid, or pills; coughing after eating or after lying down; breathing difficulties or choking episodes; troublesome or annoying cough; and sensation of something sticking in the throat or a lump in the throat. Of these 6 symptoms, 5 were in the foregut category.

Comparison of Breath Testing Techniques

Figure 15A:
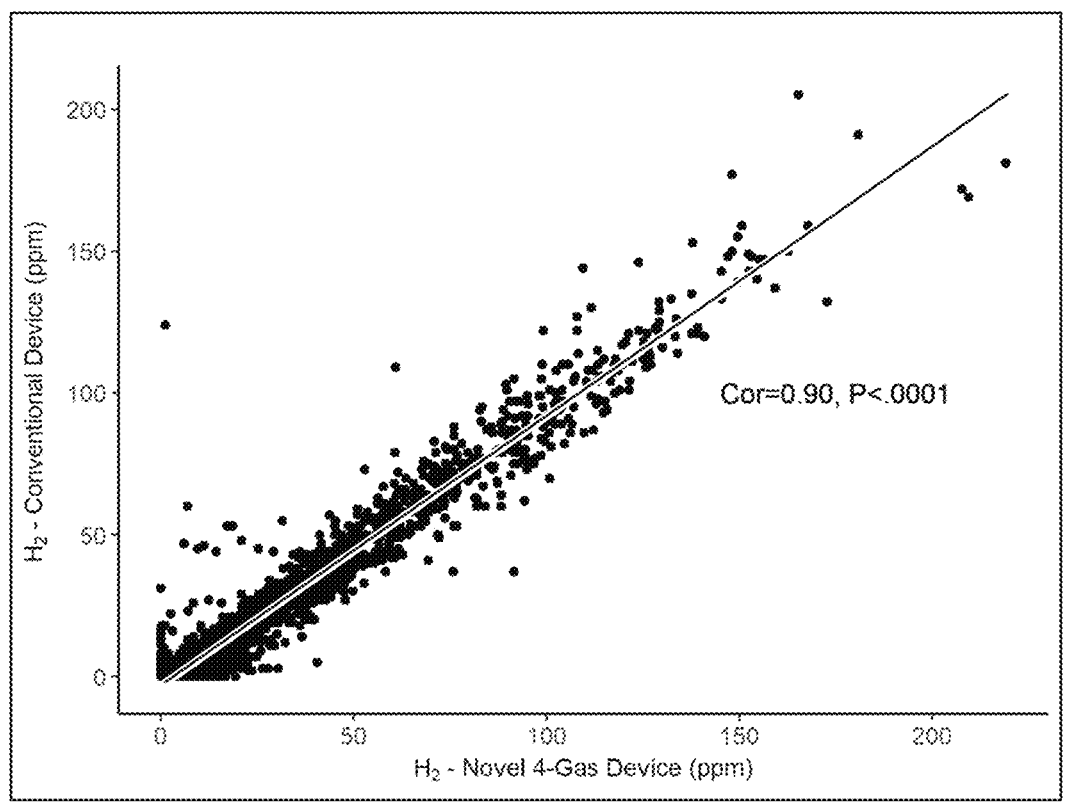
FIG. 15A depicts, in accordance with various embodiments of the present invention, a graph showing comparison data for an example of a four gas device compared to a conventional breath test instrument and in particular correlation between devices based on $H_2$-levels.
Figure 15B:
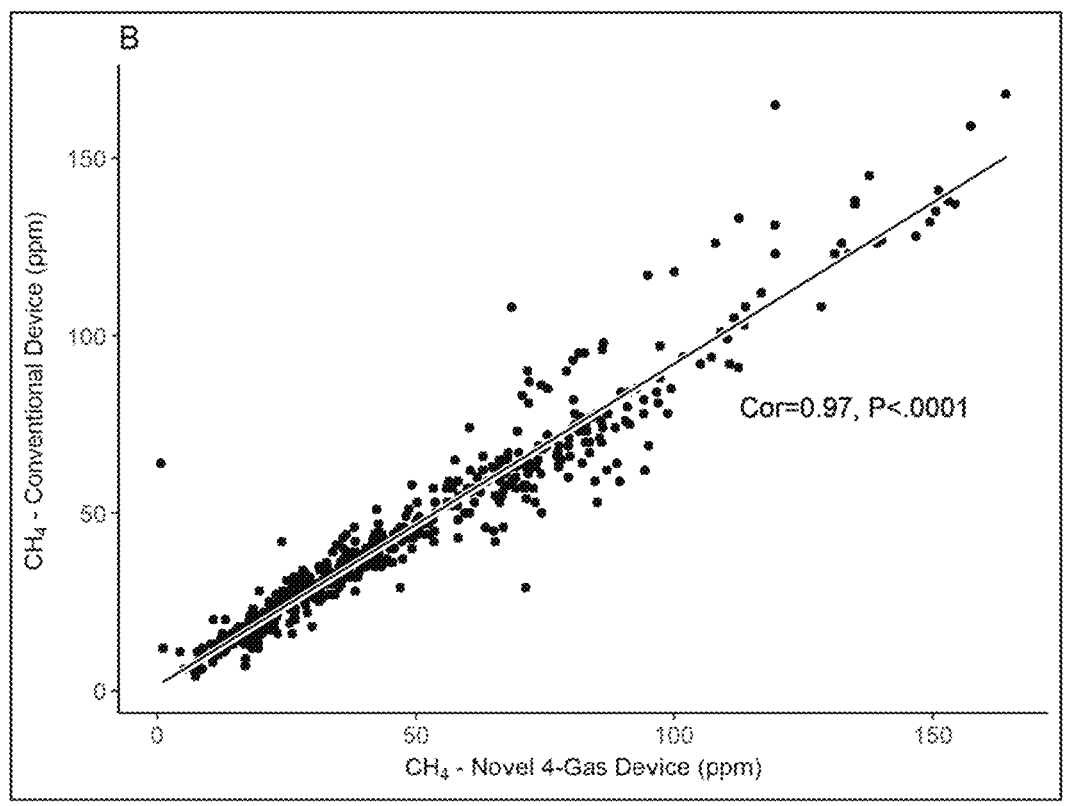
FIG. 15B depicts, in accordance with various embodiments of the present invention, a graph showing comparison data for an example of a four gas device compared to a conventional breath test instrument and in particular correlation between devices based on $CH_4$ levels $\geq 10$ ppm.

The $H_2$ and $CH_4$ results from the QuinTron instrument and the novel 4-gas device were strongly correlated as depicted in FIGS. 15A and 15B. In addition, after adjusting for the higher error level of the QuinTron, there was a moderate to substantial agreement for positive $H_2$ and $CH_4$ breath tests (Kappa=0.72 and 0.52, respectively) between the 2 instruments. Following this validation, the remainder of the analyses presented below were performed using results from the novel 4-gas device only.

Defining a Positive $H_2S$ Level

The association between $H_2S$ and IBS-D symptoms was evaluated using a using generalized linear regression, and it was found that an increase in $H_2S$ level of 1 ppm correlated with an increase in the VAS score of diarrhea by 15.8 (p=0.04) and increase in urgency with bowel movement by 16.2 (p=0.04). After assessing $H_2S$ thresholds from the 60th to 90th percentiles, the data indicated that a $H_2S$ level ≥1.2 ppm was the optimal threshold for association with diarrhea severity.

Relationship Between $H_2S$ and Diarrhea

After establishing the definition for a positive $H_2S$ breath test, symptoms were evaluated based on this threshold. In univariate analysis, the severities of diarrhea and urgency with bowel movement were significantly greater in the $H_2S$ positive group than the $H_2S$ negative group (52±32 vs. 41±31, p=0.01 and 51±32 vs. 42±32, p=0.04, respectively) (FIG. 13). Combinations of symptoms were further evaluated using the same threshold.

Figure 16:
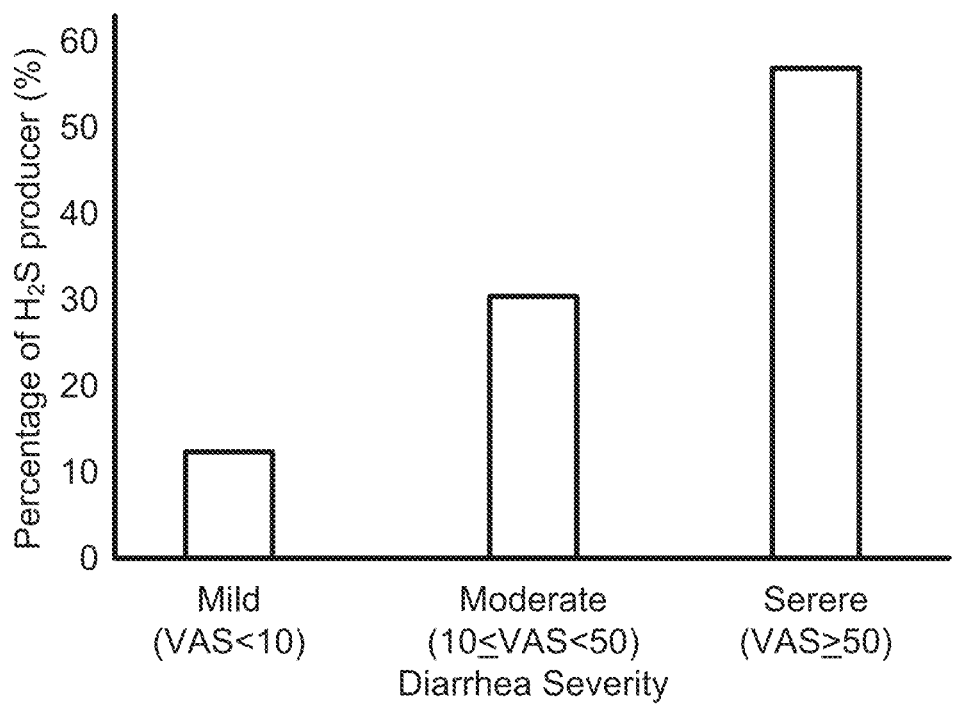
FIG. 16 depicts, in accordance with various embodiments of the present invention, a bar graph illustrating diarrhea severity in $H_2S$ positive subjects in an example study using the disclosed technology.

Diarrhea and urgency with bowel movement were significantly different between $H_2S$ positive versus negative groups (52±29 vs. 42±28, p=0.01). In addition, abdominal pain+diarrhea and abdominal pain+diarrhea+urgency with bowel movement were also significantly different as depicted in FIG. 13. There was also a statistically significant difference between the proportion of $H_2S$ positivity among subjects reporting mild diarrhea (diarrhea score of <10 on VAS), moderate diarrhea (diarrhea score ≥10 and <50), and severe diarrhea (diarrhea score ≥50) as depicted in FIG. 16. The percentage of $H_2S$ positive subjects reporting severe diarrhea (56.94%) was higher than the percentage of $H_2S$ positive subjects reporting moderate diarrhea (30.56%) and higher than the percentage of $H_2S$ positive subjects reporting mild or no diarrhea (12.50%) (p=0.01).

Gas Patterns on Breath Testing

Figure 17:
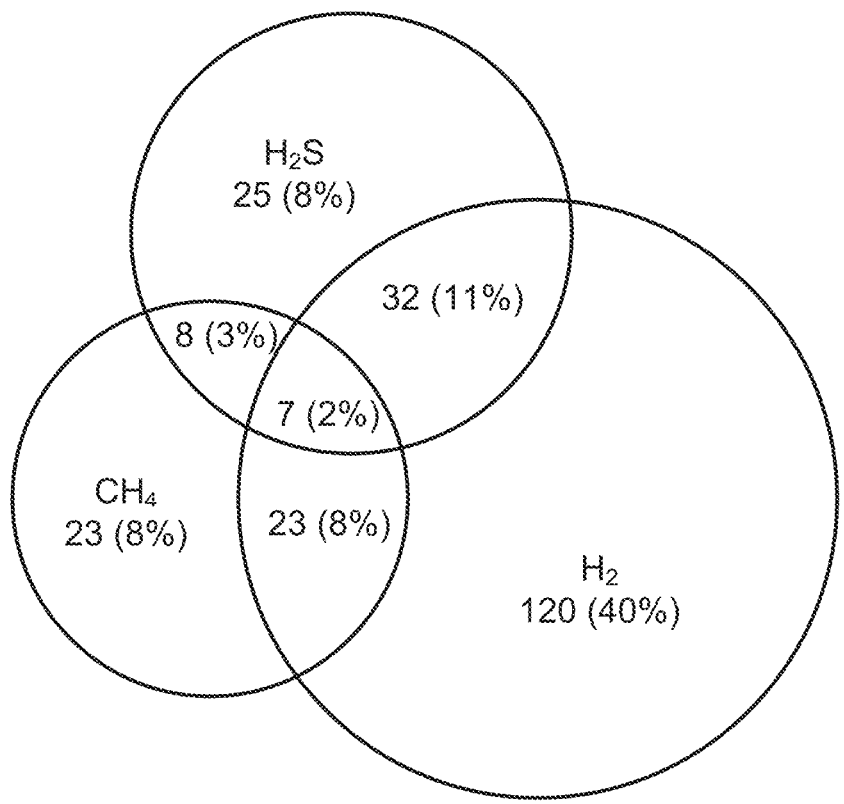
FIG. 17 depicts, in accordance with various embodiments of the present invention, a Venn diagram showing overlapping patterns of positive breath tests revealed by an example of a four gas device according to the present disclosed used in an example study.

Based on results from the novel 4-gas device, many subjects had positive $H_2$ and $CH_4$ breath tests, as shown in FIGS. 15A and 15B. There were also overlapping patterns among the breath test results, i.e. subjects who tested positive for more than one gas as depicted in FIG. 17. During conventional breath testing (i.e. performed using the QuinTron instrument), patients often exhibited "flatline" breath tests, defined as no $CH_4$ and no rise in $H_2$ [7]. When analyzed using the novel 4-gas device, 29.4% of these subjects were found not only to have detectable $H_2S$ but to meet the newly-defined threshold for a positive $H_2S$ breath test (≥1.2 ppm).

Figure 18A:
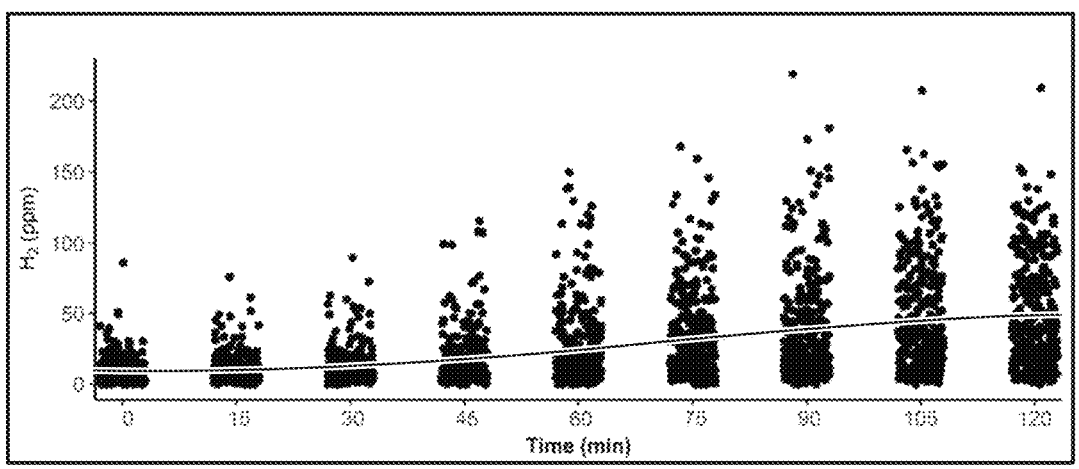
FIG. 18A depicts, in accordance with various embodiments of the present invention, a scatterplot of breath tests for an example study using the disclosed technology and particularly $H_2$ detection with a local regression line.
Figure 18B:
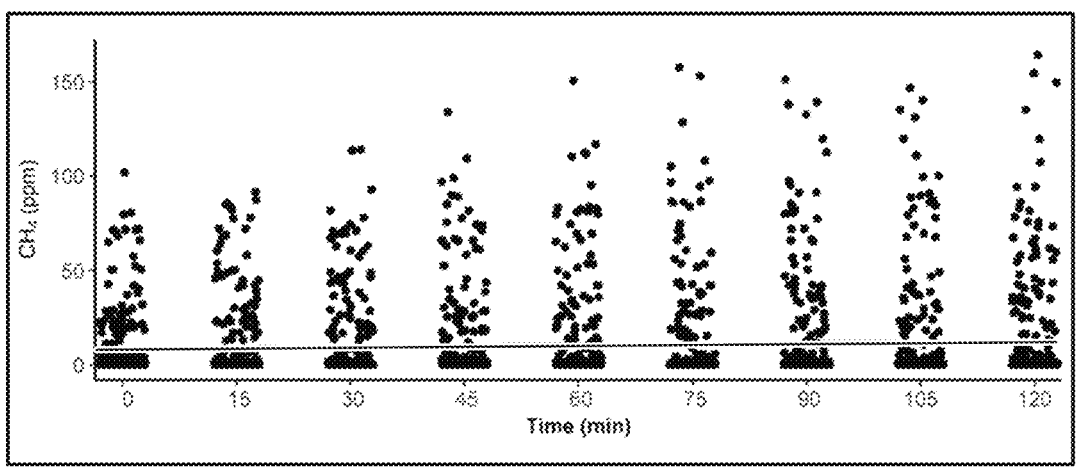
FIG. 18B depicts, in accordance with various embodiments of the present invention, a scatterplot of breath tests from an example study using the disclosed technology and particularly $CH_4$ detection with a local regression line.
Figure 18C:
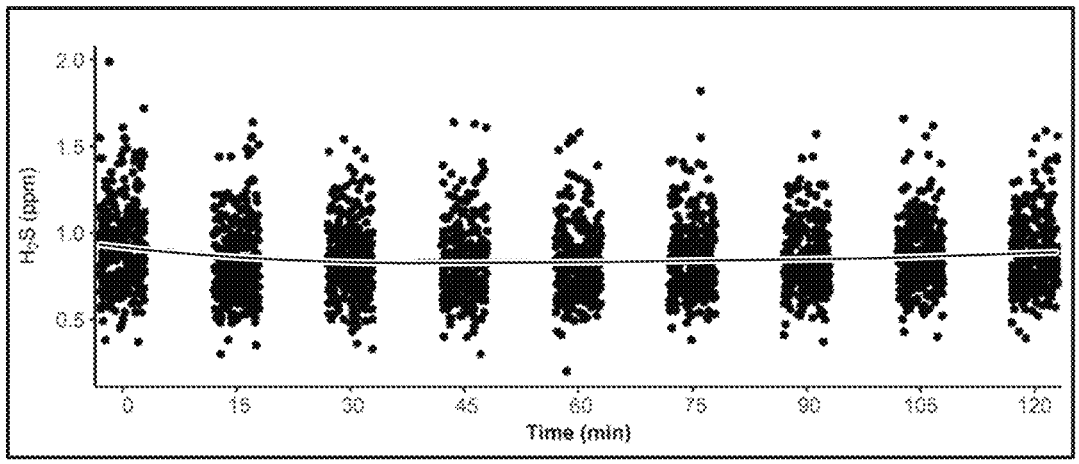
FIG. 18C depicts, in accordance with various embodiments of the present invention, a scatterplot of breath tests from an example study using the disclosed technology and particularly $H_2S$ detection with a local regression line.

The North American Consensus on breath testing recognized the distinct patterns of $H_2$ and $CH_4$ during breath testing, in that carbohydrate ingestion results in an increase in $H_2$ levels over 90-120 minutes, whereas $CH_4$ is either present or absent. This is because methanogenesis (specifically, hydrogenotrophic methanogenesis) requires a source of $H_2$, rather than carbohydrates. These patterns were also seen in this study (FIGS. 18A and 18B). As the production of $H_2S$ also required $H_2$ as a substrate rather than carbohydrates, $H_2S$ levels also remained steady following carbohydrate ingestion as depicted in FIG. 18C.

Figure 19A:
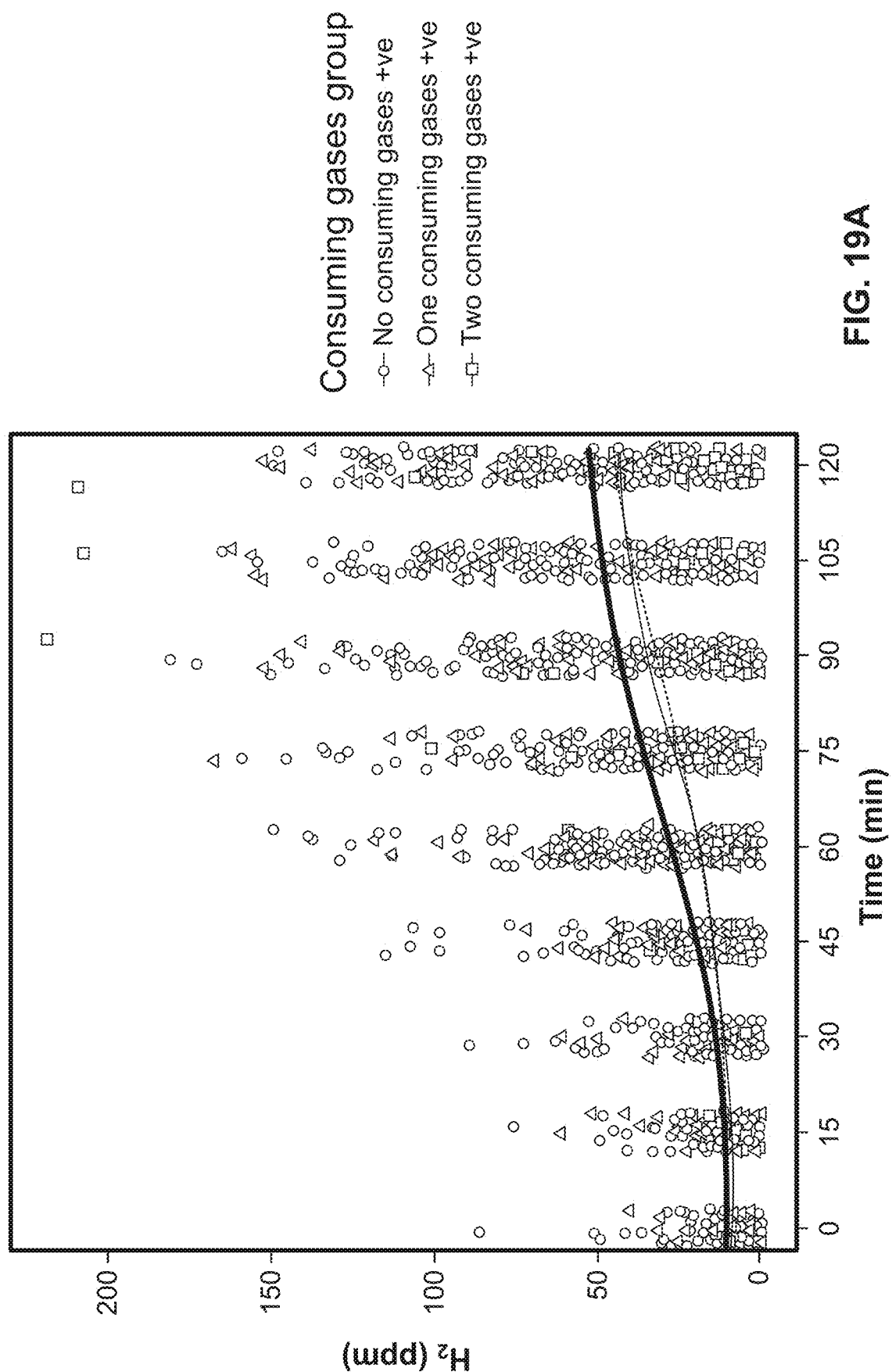
FIGS. 19A and 19B depicts in accordance with various embodiments of the present invention, bar graphs of $H_2$ consumption suggested by a breath test based on the presence of $CH_4$ and $H_2S$ from an example studying using the disclosed technology.
Figure 19B:
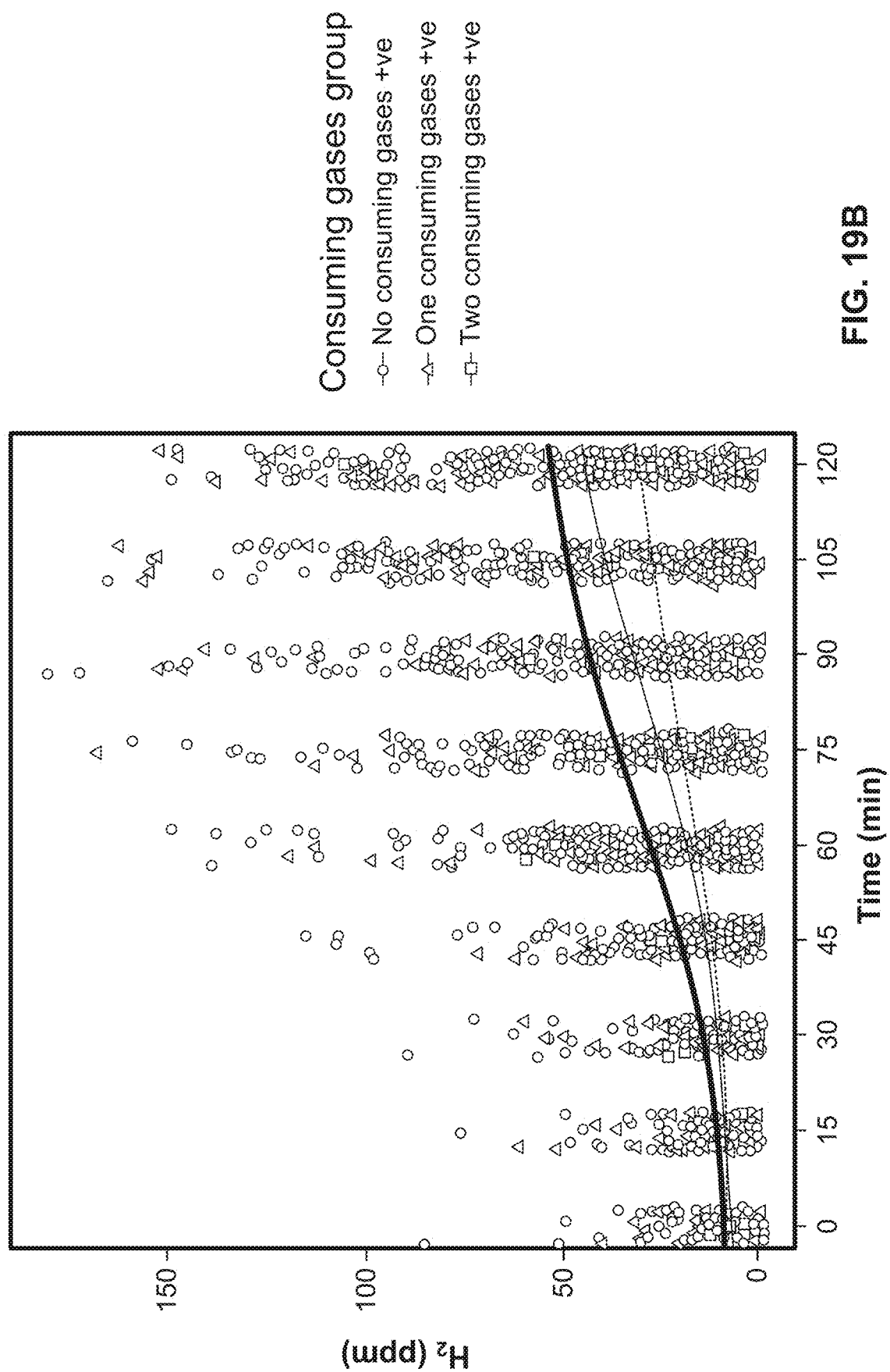

As the production of both $CH_4$ and $H_2S$ require $H_2$ as a substrate, the effects of these gases on $H_2$ levels were assessed. In this analysis, $CH_4$ and $H_2S$ were termed "consuming gases" as their production involves $H_2$ consumption. Of the study subjects, 180 were categorized as "No Consuming Gas Positive", 103 subjects were "One Consuming Gas Positive" (positive for $CH_4$ or positive for $H_2S$), and 15 were "Two Consuming Gases Positive" (positive for both $CH_4$ and $H_2S$). In this comparison, $H_2$ levels in the No Consuming Gas group were higher than in the other 2 groups, whereas the regression lines of $H_2$ in One Consuming Gas and Two Consuming Gases overlaid each other as depicted in FIG. 19A. However, $H_2$ patterns were successively lower as the number of consuming gases increased, excluding 1 outlier subject as depicted in FIG. 19B. Specifically, the cumulative $H_2$ level in the No Consuming Gas group was 56 ppm higher than in the One Consuming Gas group (p=0.04), 106 ppm higher than in the Two Consuming Gases group (p=0.09), and 62 ppm higher than when any consuming gases were positive (p=0.005).

Direct Interaction Between $CH_4$, $H_2S$, and Diarrhea

Figure 20A:
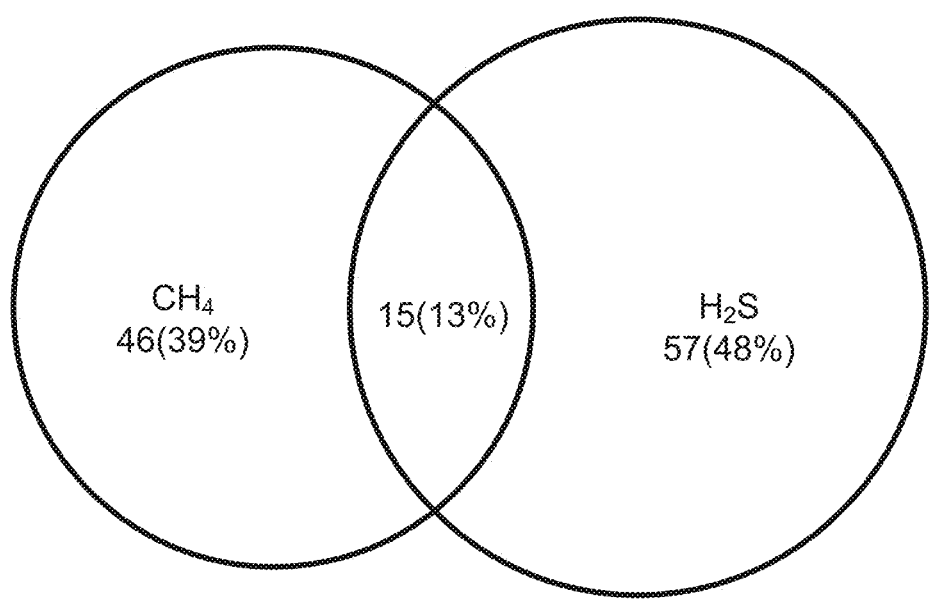
FIG. 20A depicts, in accordance with various embodiments of the present invention, a Venn diagram of $CH_4$ and $H_2S$ positive subjects from an example studying using the disclosed technology.
Figure 20B:
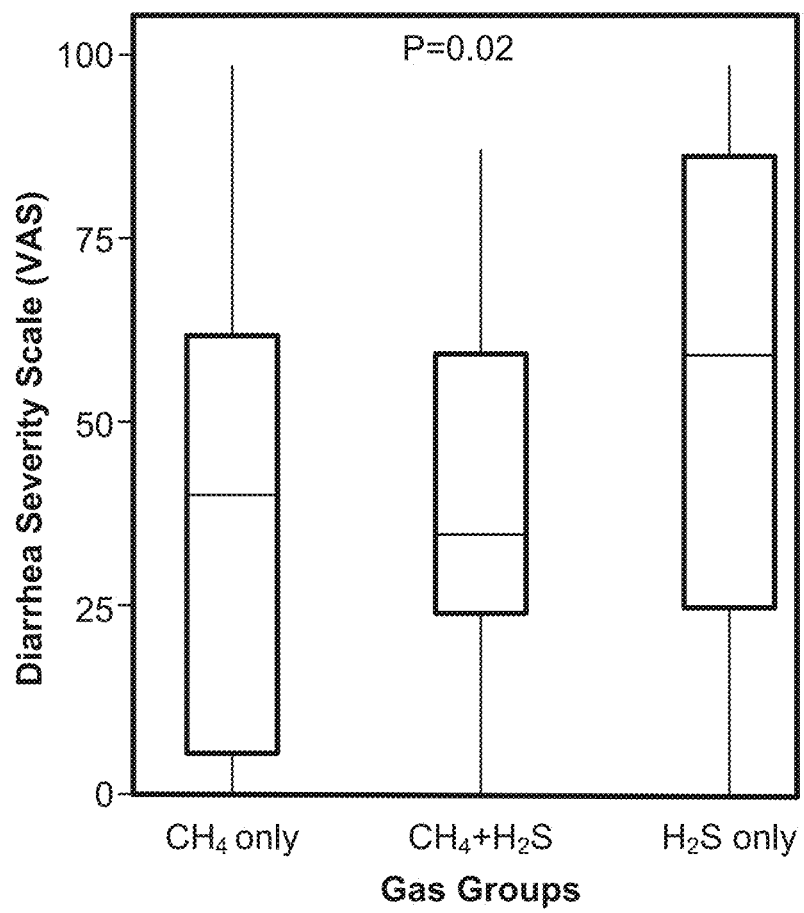
FIG. 20B depicts, in accordance with various embodiments of the present invention, a Bar graph showing the impact of $CH_4$ on diarrhea severity in the presence of $H_2S$.

As $CH_4$ is known to delay intestinal transit and to be associated with constipation rather than diarrhea 4, 8, 9, and is also known to compete with $H_2S$ for the consumption of $H_2$, the interactions between these gases were explored with respect to diarrhea. To do this, subjects who were positive for $CH_4$, $H_2S$, or both were evaluated as depicted in FIG. 20A. While $H_2S$ was associated with greater diarrhea severity, $CH_4$ appeared to be the overriding gas. Referring to FIG. 20B, subjects who were positive for $CH_4$ alone exhibited lesser diarrhea severity than those who were positive for $H_2S$ alone. Further referring to FIG. 20B, subjects who were positive for both $CH_4$ and $H_2S$ exhibited lesser severity of diarrhea than those who were positive for $H_2S$ alone.

Analysis

This study demonstrated for the first time that a 4-gas breath testing device, based on the disclosed technology, which can detect $H_2S$ in addition to $H_2$, $CH_4$ and $CO_2$ adds significantly to the utility of clinical breath testing. First, it was found that humans have detectable and variable $H_2S$ levels on their breath. Importantly, $H_2S$ was found to be associated with diarrhea as well as other related symptoms not previously correlated with $H_2$ alone, and the inclusion of $H_2S$ explained at least a subset of 'flatline' breath tests. The addition of $H_2S$ also enhanced the understanding of $H_2$ levels and the interaction with $CH_4$, allowing for a more complete breath test.

While these findings for $CH_4$ are interesting, clinical breath testing was originally based on the measurement of $H_2$ gas alone. However, no studies have clearly defined a link between the level of $H_2$ production and clinical symptoms, which has led to skepticism regarding the clinical significance of breath testing. Some critics even suggest that breath testing is merely determining transit time and cannot be used to diagnose SIBO [14], [15]. Part of the reason for the skepticism surrounding breath testing may stem from the fact that the existing test is incomplete, and thus can generate inconclusive results (e.g. flatline tests). Measuring $H_2$ and $CH_4$ alone provides an incomplete understanding of the complex microbial interactions occurring within the intestinal tract.

While $H_2$ is produced during fermentation, it is also consumed by other organisms. There are 3 disposition pathways for $H_2$. Methanogens (e.g. M. smithii) use 4 molecules of $H_2$ to produce 1 molecule of $CH_4$ [6]. The second pathway involves the use of 5 molecules of $H_2$ by sulfate-reducing organisms to produce 1 molecule of $H_2S$ [6]. A third and minor pathway is the disposition of $H_2$ by acetogens, which is not a gas-producing pathway. This in and of itself should suggest that there is no way to reliably know the true level of $H_2$ production in the gut. Furthermore, such complex interactions among various gut microbes explain the challenges of finding direct linear associations between absolute $H_2$ levels on breath testing and both intestinal bacterial load and clinical symptoms. Thus, measurement of $H_2S$ in addition to $H_2$ and $CH_4$ is critical to a more complete understanding of the microbial-host interaction.

Another common problem during breath testing is the "flatline" pattern. In this case, the clinical breath test shows a steady level of $H_2$ throughout the test and no measurable $CH_4$. One explanation would be that the gut is completely devoid of $CH_4$- and $H_2$-producing organisms. However, that is highly unlikely. In the current study, it was demonstrated that in these "flatline" breath tests $H_2S$ is frequently present, suggesting the consumption of $H_2$ by sulfate-reducing organisms leads to an inaccurate assessment of $H_2$ production.

Additionally, measuring $H_2$ levels alone provide an incomplete understanding of the clinical picture. For example, studies of SIBO have suggested a connection between a positive breath test and IBS 10, 11, but there is no clear relationship between the degree of any symptom and $H_2$ on breath test. In this study, $H_2S$ was found to be more common than expected, with 24% of subjects testing positive for $H_2S$. In addition, diarrhea was specifically associated with the presence and level of $H_2S$ on the breath test.

These results further suggest there is a balance-counterbalance effect between $CH_4$ and $H_2S$. First, since the production of these gases requires the consumption of $H_2$, it was found that the levels of $H_2$ were dependent on whether $CH_4$, $H_2S$, or both were present. This finding is important because it suggests that clinicians cannot rely solely on $H_2$ measurements, as they are affected by $CH_4$ and $H_2S$. The second important finding is that $CH_4$ appears to counterbalance the effect of $H_2S$ on diarrhea severity. $CH_4$ is known to be associated with, and a cause of, constipation [9]. On the other hand, $H_2S$ is known to have a toxic effect on the epithelium [16]. Thus, it appears that $CH_4$ has an overriding effect on diarrhea severity even when $H_2S$ is present.

In conclusion, this study is the first to demonstrate the validity and utility of a novel 4-gas device for clinical breath testing in subjects being assessed for SIBO. Based on these results, there is a clear benefit to the addition of $H_2S$ measurement to breath testing, as this provides the most comprehensive analysis to date of human intestinal microbial gas interactions in vivo. In addition, measurement of $H_2S$ answers important questions about breath testing, such as flatline tests. Finally, $H_2S$ appears to be associated with a diarrhea phenotype and is more predictive of diarrhea-related symptoms than $H_2$. The study demonstrates the importance of measuring all 4 gases during breath testing.

Selected Embodiments

Although the above description and the attached claims disclose a number of embodiments of the present invention, other alternative aspects of the invention are disclosed in the following further embodiments.

A system for testing the breath of a patient for the concentration of various gases comprising:
    a breath collector;
    a gas inlet connectable to the breath collector
    a gas exhaust;
    a manifold comprising a gas flow path in gaseous communication with the gas inlet and the gas exhaust;
    at least one gas sensor configured to output sensor data relating to a concentration of a gas passing through the gas flow path;
    a heating element in thermal communication with the manifold;

a temperature sensor configured to output temperature data relating to a temperature of the manifold;

a control system comprising one or more processors and a memory for determining a concentration of gases based on the output sensor data; and a display that outputs the determined concentration of gases.

The system wherein the at least one gas sensor comprises at least one of a $CH_4$ sensor, a $CO_2$ sensor, an $H_2$ sensor, or an $H_2S$ sensor.

The system wherein the at least one gas sensor comprises a $CO_2$ sensor, an $H_2$ sensor, and $H_2S$ sensor, positioned in series along the gas flow path and the gas flow path comprises a single channel in the manifold.

The system wherein one a first baffle is position adjacent the $H_2$ sensor and a second baffle is positioned adjacent to the $H_2S$ sensor and wherein the first and second baffle are sized and shaped to facilitate gas exchange with the $H_2S$ sensor and the $H_2$ sensor.

The system further comprising a pump configured to pump gas through the gas flow path based on feedback from a flow meter configured to detect a flow rate through the gas flow path.

The system wherein the temperature sensor is a thermistor connected to a printed circuit board.

The system wherein the heating element is connected to the printed circuit board.

The system, wherein the heating element comprises a trace printed on the printed circuit board.

The system wherein the heating element comprises a plurality of heating elements, and wherein each of the plurality of heating elements is configured to heat one of a set of zones of the manifold.

The system wherein the temperature sensor comprises a plurality of temperature sensors and wherein each of the plurality of temperature sensors is configured to output temperature data relating to one of the set of zones of the manifold.

The system wherein the control system is configured to maintain a minimum temperature of the manifold by energizing the heating element based on data output from the temperature sensor.

The system wherein the manifold comprises a metal block and wherein the gas flow path is constructed through the metal block.

The system wherein the manifold comprises a thermally conductive material.

The system wherein the thermally conductive material comprises stainless steel or copper.

The system wherein the gas flow path comprises a baffle positioned adjacent to the at least one gas sensor.

The system wherein the minimum temperature is between 38 and 41 degrees Celsius.

The system wherein the minimum temperature is 40 degrees Celsius.

The system wherein the control system is configured to determine an indication of whether a patient has SIBO based on the output sensor data.

The system wherein the output sensor data comprises data output from a $CH_4$ sensor, a $CO_2$ sensor, an $H_2$ sensor, and an $H_2S$ sensor.

The system wherein the control system is further configured to output an indication of diarrhea of the patient if the output sensor data indicates an increase in $H_2S$ level.

The system wherein the control system is further configured to output a positive indication of SIBO if the output sensor data indicates that an $H_2S$ level increases and a $CH_4$ and $H_2$ breath gases levels did not increase during a lactulose breath test.

A method of sensing gas concentration in exhaled breath, the method comprising:
receiving a batch of exhaled breath from a patient;
heating the batch of exhaled breath to a temperature above 37 degrees Celsius while pumping the air through a flow path at a constant flow rate;
sensing gas concentrations in the flow path using a set of electrochemical sensors; and
displaying the gas concentrations.

The method, wherein the gas concentrations comprise a $CH_4$, a $CO_2$, $H_2$, and a $H_2S$ concentration.

The method, wherein the flow path is routed through a manifold.

The method, wherein heating the batch of breath comprises maintaining the manifold at a temperature above 37 degrees Celsius.

The method, wherein the gas concentrations comprise at least $CH_4$, and $H_2$ and the control system is further configured to determine an indication of whether the patient has SIBO based on the gas concentrations.

A method of sensing gas concentration in exhaled breath, the method comprising:
receiving a batch of exhaled breath from a patient;
heating the batch of exhaled breath to a temperature above 37 degrees Celsius while pumping the air through a flow path at a constant flow rate;
sensing gas concentrations in the flow path using a set of electrochemical sensors; and
displaying the gas concentrations.

The method wherein the gas concentrations comprise a $CH_4$, a $CO_2$, $H_2$, and a $H_2S$ concentration.

The method wherein the flow path is routed through a manifold.

The method wherein heating the batch of breath comprises maintaining the manifold at a temperature above 37 degrees Celsius.

The method wherein the gas concentrations comprise at least $CH_4$, and $H_2$ and the control system is further configured to determine an indication of whether the patient has SIBO based on the gas concentrations.

REFERENCES

1. Gasbarrini A, Corazza G R, Gasbarrini G, et al. Methodology and indications of $H_2$-breath testing in gastrointestinal diseases: the Rome Consensus Conference. Aliment Pharmacol Ther 2009; 29 Suppl 1:1-49.
2. Rezaie A, Buresi M, Lembo A, et al. Hydrogen and Methane-Based Breath Testing in Gastrointestinal Disorders: The North American Consensus. The American Journal Of Gastroenterology 2017; 112:775.
3. Pimentel M. Review article: potential mechanisms of action of rifaximin in the management of irritable bowel syndrome with diarrhoea. Aliment Pharmacol Ther 2016; 43 Suppl 1:37-49.
4. Kim G, Deepinder F, Morales W, et al. Methanobrevibacter *smithii* is the predominant methanogen in patients with constipation-predominant IBS and methane on breath. Dig Dis Sci 2012; 57:3213-8.
5. Chatterjee S, Park S, Low K, et al. The degree of breath methane production in IBS correlates with the severity of constipation. Am J Gastroenterol 2007; 102:837-41.
6. Krajmalnik-Brown R, Ilhan Z-E, Kang D-W, et al. Effects of Gut Microbes on Nutrient Absorption and Energy Regulation. Nutrition in clinical practice: official publication of the American Society for Parenteral and Enteral Nutrition 2012; 27:201-214.
7. Rezaie A, Buresi M, Lembo A, et al. Hydrogen and Methane-Based Breath Testing in Gastrointestinal Disorders: The North American Consensus. Am J Gastroenterol 2017; 112:775-784.
8. Pimentel M, Lin H C, Enayati P, et al. Methane, a gas produced by enteric bacteria, slows intestinal transit and augments small intestinal contractile activity. Am J Physiol Gastrointest Liver Physiol 2006; 290:G1089-95.
9. Kunkel D, Basseri R J, Makhani M D, et al. Methane on breath testing is associated with constipation: a systematic review and meta-analysis. Dig Dis Sci 2011; 56:1612-8.
10. Rezaie A, Pimentel M, Rao S S. How to Test and Treat Small Intestinal Bacterial Overgrowth: an Evidence-Based Approach. Curr Gastroenterol Rep 2016; 18:8.
11. Ponziani F R, Gerardi V, Gasbarrini A. Diagnosis and treatment of small intestinal bacterial overgrowth. Expert Rev Gastroenterol Hepatol 2016; 10:215-27.
12. Turnbaugh P J, Ley R E, Hamady M, et al. The Human Microbiome Project. Nature 2007; 449:804.
13. The Human Microbiome Project C. Structure, function and diversity of the healthy human microbiome. Nature 2012; 486:207.
14. Lin E C, Massey B T. Scintigraphy Demonstrates High Rate of False-positive Results From Glucose Breath Tests for Small Bowel Bacterial Overgrowth. Clin Gastroenterol Hepatol 2016; 14:203-8.
15. Yu D, Cheeseman F, Vanner S. Combined oro-caecal scintigraphy and lactulose hydrogen breath testing demonstrate that breath testing detects oro-caecal transit, not small intestinal bacterial overgrowth in patients with IBS. Gut 2011; 60:334-40.
16. Beaumont M, Andriamihaja M, Lan A, et al. Detrimental effects for colonocytes of an increased exposure to luminal hydrogen sulfide: The adaptive response. Free Radical Biology and Medicine 2016; 93:155-164.
17. Pimentel M, Chang C, Chua K S, et al. Antibiotic treatment of constipation-predominant irritable bowel syndrome. Dig Dis Sci 2014; 59:1278-85.
18. Campieri M, Gionchetti P. Bacteria as the cause of ulcerative colitis. Gut 2001; 48:132-135.
19. Pimentel M. A New IBS Solution: Bacteria—The Missing Link in Treating Irritable Bowel Syndrome: Health Point Press, 2006.

—Computer & Hardware Implementation of Disclosure

It should initially be understood that the disclosure herein may be implemented with any type of hardware and/or software, and may be a pre-programmed general purpose computing device and/or control system comprising one or more processors and a memory. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively, or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSIONS

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A system configured to determine concentrations of various gases using multiple gas sensors with one breath sample from a patient, the system comprising:
   a mouthpiece into which the patient blows;
   a breath collector configured to receive the patient's breath through the mouthpiece coupled to the breath collector;
   a gas inlet connectable to the breath collector;
   a gas exhaust;
   a manifold comprising a gas flow path in gaseous communication with the gas inlet and the gas exhaust;
   the multiple gas sensors configured to measure concentrations of various gases including $CH_4$, $CO_2$, $H_2$, and $H_2S$ at once with the one breath sample, each gas sensor configured to output sensor data relating to a concentration of a different gas passing through the gas flow path, wherein the multiple gas sensors comprise a $CH_4$ sensor, a $CO_2$ sensor, an $H_2$ sensor, and an $H_2S$ sensor,
   wherein the $CH_4$ sensor is separate from the manifold, and wherein the $CO_2$ sensor, the $H_2$ sensor, and the $H_2S$ sensor are positioned in series along the gas flow path comprising a single channel in the manifold;
   wherein the gas exhaust opens to outside of the manifold, wherein the $CH_4$ sensor is connected by a pipe to the gas exhaust;
   a heating element in thermal communication with the manifold;
   a temperature sensor configured to output temperature data relating to a temperature of the manifold;
   a control system comprising one or more processors and a memory for determining concentrations of gases based on the output sensor data, the output sensor data comprising data output from the $CH_4$ sensor, the $CO_2$ sensor, the $H_2$ sensor, and the $H_2S$ sensor; and
   a display that outputs the determined concentration of gases.

2. The system of claim 1, wherein a first baffle is positioned adjacent to the $H_2$ sensor and a second baffle is positioned adjacent to the $H_2S$ sensor and wherein the first and second baffles are sized and shaped to facilitate gas exchange with the $H_2S$ sensor and the $H_2$ sensor.

3. The system of claim 2, wherein the heating element comprises a plurality of heating elements, and wherein each of the plurality of heating elements is configured to heat one of a set of zones of the manifold.

4. The system of claim 3, wherein the temperature sensor comprises a plurality of temperature sensors and wherein each of the plurality of temperature sensors is configured to output temperature data relating to one of the set of zones of the manifold.

5. The system of claim 1, further comprising a pump configured to pump gas through the gas flow path based on feedback from a flow meter configured to detect a flow rate through the gas flow path.

6. The system of claim 1, wherein the temperature sensor is a thermistor connected to a printed circuit board.

7. The system of claim 6, wherein the heating element is connected to the printed circuit board.

8. The system of claim 6, wherein the heating element comprises a trace printed on the printed circuit board.

9. The system of claim 1, wherein the control system is configured to maintain a minimum temperature of the manifold by energizing the heating element based on data output from the temperature sensor.

10. The system of claim 9, wherein the minimum temperature is 40 degrees Celsius or between 38 and 41 degrees Celsius.

11. The system of claim 1, wherein the manifold comprises a metal block and wherein the gas flow path is constructed through the metal block.

12. The system of claim 1, wherein the manifold comprises a thermally conductive material, stainless steel, or copper.

13. The system of claim 1, wherein the gas flow path comprises a baffle positioned adjacent to at least one gas sensor of the multiple gas sensors.

14. The system of claim 1, wherein the control system is configured to determine an indication of whether the patient has small intestine bacterial overgrowth (SIBO) based on the output sensor data comprising the concentrations of $CH_4$, $CO_2$, $H_2$, and $H_2S$ measured at once with the one breath sample received from the patient.

15. The system of claim 1, wherein integration of the manifold and the multiple gas sensors allows for measuring the concentrations of the various gases including $CH_4$, $CO_2$, $H_2$, and $H_2S$ at once in the same system.

16. The system of claim 1, wherein the control system is further configured to output an indication of diarrhea of the patient if the output sensor data indicates an increase in $H_2S$ level.

17. The system of claim 1, wherein the control system is further configured to output a positive indication of SIBO in response to the output sensor data indicating that an $H_2S$ level increased and a $CH_4$ and $H_2$ breath gases levels did not increase during a lactulose breath test.

18. The system of claim 1, further comprising a user interface configured to receive, from the patient, which of predefined categories of symptoms the patient is experiencing, the predefined categories comprising bloating, constipation, and diarrhea.

19. The system of claim 1, wherein the control system is configured to:
cause the memory to store information about time and content of meals consumed by the patient prior to SIBO testing; and
cause the display to output correlations between consumed foods and symptoms and the determined concentration of gases.

20. The system of claim 1, wherein the system is a portable handheld system.

21. The system of claim 1, further comprising a flow meter configured to provide feedback to the patient regarding a proper strength of breath in response to the breath received through the mouthpiece.

22. A method of sensing gas concentrations in exhaled breath for small intestine bacterial overgrowth (SIBO) testing, the method performed by the system of claim 1 and comprising:
receiving, by the breath collector, a single batch of exhaled breath from a patient via the mouthpiece;
heating, by the heating element, the single batch of exhaled breath to a temperature above 37 degrees Celsius while pumping the air through the gas flow path at a constant flow rate;
sensing, by the $CH_4$ sensor, $CO_2$ sensor, $H_2$ sensor, and $H_2S$ sensor, gas concentrations of $CH_4$, $CO_2$, $H_2$, and $H_2S$ at once to determine whether the patient has SIBO; and
displaying, on the display, the gas concentrations.

23. The method of claim 22, wherein heating the single batch of breath comprises maintaining the manifold at the temperature above 37 degrees Celsius.

24. The method of claim 22, further comprising determining, by the control system, an indication of whether the patient has SIBO based on the gas concentrations measured at once from the single batch of breath received from the patient.

25. The method of claim 22, further comprising receiving, via a user interface from the patient, which of predefined categories of symptoms the patient is experiencing, the predefined categories comprising bloating, constipation, and diarrhea.

26. The method of claim 22, further comprising:
storing, in the memory, information about time and content of meals consumed by the patient prior to SIBO testing; and
outputting, via the display, correlations between consumed foods and symptoms and the determined concentration of gases.

* * * * *